United States Patent
Chen et al.

(10) Patent No.: US 9,725,749 B2
(45) Date of Patent: Aug. 8, 2017

(54) GLYCOSIDE HYDROLASES HAVING MULTIPLE HYDROLASE ACTIVITIES

(75) Inventors: Zhiwei Chen, Castro Valley, CA (US); Gregory D. Friedland, San Francisco, CA (US); Swapnil R. Chhabra, Oakland, CA (US); Dylan C. Chivian, Albany, CA (US); Blake A. Simmons, San Francisco, CA (US)

(73) Assignees: The Regents of the University of California, Oakland, CA (US); Sandia Corporation, Livermore, CA (US)

( * ) Notice: Subject to any disclaimer, the term of this patent is extended or adjusted under 35 U.S.C. 154(b) by 323 days.

(21) Appl. No.: 14/114,990

(22) PCT Filed: May 1, 2012

(86) PCT No.: PCT/US2012/036007
§ 371 (c)(1),
(2), (4) Date: Feb. 13, 2014

(87) PCT Pub. No.: WO2012/151214
PCT Pub. Date: Nov. 8, 2012

(65) Prior Publication Data
US 2014/0154752 A1  Jun. 5, 2014

Related U.S. Application Data

(60) Provisional application No. 61/481,642, filed on May 2, 2011.

(51) Int. Cl.
C12N 9/38 (2006.01)
C12P 19/14 (2006.01)
C12N 9/42 (2006.01)
C12P 19/02 (2006.01)

(52) U.S. Cl.
CPC .......... *C12P 19/14* (2013.01); *C12N 9/2434* (2013.01); *C12N 9/2437* (2013.01); *C12P 19/02* (2013.01); *C12Y 302/01004* (2013.01)

(58) Field of Classification Search
CPC ........................................................ C12N 9/48
USPC ........................................................ 435/207
See application file for complete search history.

(56) References Cited

U.S. PATENT DOCUMENTS 5,962,258 A    10/1999  Mathur et al.
7,422,876 B2    9/2008  Short et al.
2008/0233175 A1  9/2008  Steer et al.

FOREIGN PATENT DOCUMENTS

WO    2010/124266 A2    10/2010

OTHER PUBLICATIONS

The International Search Report and Written Opinion from PCT/US2012/036007, dated Jul. 27, 2012.
Chhabra et al.; "Regulation of the Endo-Acting Glycosyl Hydrolases in the Hyperthermophilic Bacterium *Thermotoga maritima* Grown on Glucan- and Mannan-Based Polysaccharides"; *Appl. Environ. Microbiol.* 68(2):545-554 (2002).
Mahadevan et al.; "Site-Directed Mutagenesis and CBM Engineering of Cel5A (*Thermotoga maritima*)"; *FEMS Microbiol. Lett*; 287:205-211 (2008).
Pereira et al.; "Biochemical Characterization and Crystal Core Structure of Engoglucanase Cel5A from the Hyperthermophilic *Thermotoga maritima*"; *J. Struct. Biol*.; 172:372-379 (2010).
Third Party Observation filed in PCT/US2012/036007, submitted Jul. 2, 2013 (2 pages).

*Primary Examiner* — Tekchand Saidha
(74) *Attorney, Agent, or Firm* — Kilpatrick Townsend & Stockton LLP

(57) ABSTRACT

Glycoside hydrolases having at least two different hydrolytic activities are provided. In one embodiment, an isolated recombinant hydrolase having at least two activities selected from a group including asparagine derivatives, glutamine derivatives, and histidine derivatives is provided. Further, a method of generating free sugars from a mixture comprising asparagine derivatives, glutamine derivatives, and histidine derivatives is provided.

8 Claims, 6 Drawing Sheets

SEQUENCE LISTING

<160> NUMBER OF SEQ ID NOS: 12

<210> SEQ ID NO 1
<211> LENGTH: 317
<212> TYPE: PRT
<213> ORGANISM: Thermotoga maritima
<220> FEATURE:
<223> OTHER INFORMATION: Thermotoga maritima strain MSB8 endoglucanase,
      Cel5A, Cel5ATma, locus TM_1751, locus B72216

<400> SEQUENCE: 1

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

-continued

```
Val Thr Ile His Tyr Tyr Asn Pro Phe Glu Phe Thr His Gln Gly Ala
        195                 200                 205
Glu Trp Val Glu Gly Ser Glu Lys Trp Leu Gly Arg Lys Trp Gly Ser
    210                 215                 220
Pro Asp Asp Gln Lys His Leu Ile Glu Glu Phe Asn Phe Ile Glu Glu
225                 230                 235                 240
Trp Ser Lys Lys Asn Lys Arg Pro Ile Tyr Ile Gly Glu Phe Gly Ala
                245                 250                 255
Tyr Arg Lys Ala Asp Leu Glu Ser Arg Ile Lys Trp Thr Ser Phe Val
            260                 265                 270
Val Arg Glu Met Glu Lys Arg Arg Trp Ser Trp Ala Tyr Trp Glu Phe
        275                 280                 285
Cys Ser Gly Phe Gly Val Tyr Asp Thr Leu Arg Lys Thr Trp Asn Lys
    290                 295                 300
Asp Leu Leu Glu Ala Leu Ile Gly Gly Asp Ser Ile Glu
305                 310                 315
```

<210> SEQ ID NO 2
<211> LENGTH: 954
<212> TYPE: DNA
<213> ORGANISM: Thermotoga maritima
<220> FEATURE:
<223> OTHER INFORMATION: Thermotoga maritima strain MSB8 endoglucanase, Cel5A, Cel5ATma, locus TM_1751, locus B72216 CDS

<400> SEQUENCE: 2

```
atggggttg atccgtttga gcgtaataaa attctgggcc gcggtattaa tatcggcaac    60
gcactggagg ctccgaatga aggtgattgg ggcgtggtta ttaaggatga attcttcgat   120
attatcaaag aagcgggatt tagccatgtg cgtattccga ttcgttggtc gactcatgcc   180
tatgcatttc cgccatacaa aattatggat cgcttttca acgtgtgga cgaagttatt     240
aacggtgccc tgaaacgcgg actggccgtt gttattaata tccaccacta tgaagagctg   300
atgaatgatc ctgaagaaca taagaacgc tttctggcac tgtggaaaca gattgcggac    360
cgttataaag attatccgga aactctgttt ttcgaaattc tgaacgagcc gcatgggaac   420
ctgacgccgg aaaaatggaa tgaactgctg aagaagctc tgaaagtaat ccgttcgatt    480
gacaagaaac ataccatcat tattggcacc gccgaatggg gtggtatcag tgcactggaa   540
aaactgtcag ttccgaagtg ggagaaaaac tccattgtga cgattcatta ttataacccg   600
tttgagttta cccaccaggg ggcagaatgg gtggaaggca cgaaaaatg ctgggccgt    660
aaatggggta gtcctgatga tcaaaaacac ctgattgaag agtttaactt catcgaagag   720
tggtcaaaaa agaataaacg cccgatttat attggcgagt tcggtgccta tcgcaaagct   780
gatctggaat cgcgtattaa atggacaagt tttgttgtac gtgaaatgga aaagcgccgt   840
tggtcctggg cctattggga attctgtagc ggttttggtg tctacgatac gctgcgcaaa   900
acttggaaca agatctgct ggaagcctg attggcggtg acagtatcga ataa            954
```

<210> SEQ ID NO 3
<211> LENGTH: 488
<212> TYPE: PRT
<213> ORGANISM: Epidinium ecaudatum
<220> FEATURE:
<223> OTHER INFORMATION: rumen anaerobic protozoan Epidinium ecaudatum cellulase family 5 protein (partial), Cel5AEec, cmc-06

<400> SEQUENCE: 3

```
Lys Thr Ala Ile Glu Thr Val Asn Asp Met Gly Leu Gly Trp Asn Leu
  1               5                  10                  15

Gly Asn Thr Phe Asp Cys Phe Gly Thr Trp Lys Glu Ile Lys Thr Pro
             20                  25                  30

Asp Asp Gln Ile Thr Met Trp Gly Asn Val Val Pro Thr Glu Ala Met
             35                  40                  45

Val Thr Thr Ile Lys Lys Tyr Gly Phe Lys Thr Val Arg Phe Pro Val
 50                  55                  60

Thr Trp Met Asn Phe Met Asp Glu Ser Gly Lys Val Lys Ala Glu Trp
 65                  70                  75                  80

Met Ala Arg Val Lys Glu Val Val Asp Trp Ile Val Lys Ala Gly Leu
                 85                  90                  95

Tyr Cys Ile Leu Asn Val His His Asp Gly Val Ser Gly Asn Trp Leu
                100                 105                 110

Ala Gln Gly Ala His Val Lys Ala Arg Tyr Val Thr Leu Trp Thr Gln
            115                 120                 125

Ile Ala Thr Glu Phe Lys Asp Tyr Asp His Leu Val Phe Glu Ser
            130                 135                 140

Met Asn Glu Val Glu Tyr Lys Asn Gly Asn Ser Phe Asp Tyr Asn Ser
145                 150                 155                 160

Leu Leu Thr Leu Thr Gln Ala Phe Val Asp Thr Val Arg Gly Leu Gly
                165                 170                 175

Gly Lys Asn Ser Asp Arg Leu Leu Leu Ile Ser Gly Met Asn Thr Asn
            180                 185                 190

Leu Glu Asn Thr Cys Ser Ser Ser Tyr Lys Met Pro Thr Asp Lys Ala
            195                 200                 205

Asn Lys Leu Ala Ile Ser Ile His Tyr Tyr Leu Pro Pro Gln Phe Thr
            210                 215                 220

Val Glu Ser Asp Lys Asn Pro Trp Thr Trp Thr Asp Asp Gln Gly Val
225                 230                 235                 240

Val His Glu Ile Thr Pro Leu Gln Lys Trp Gly Asp Glu Gly Asn Tyr
                245                 250                 255

Gln Glu Met Val Thr Asn Phe Glu Thr Met Lys Lys Ala Phe Val Asp
            260                 265                 270

Lys Gly Ile Pro Val Ile Leu Gly Glu Val Gly Val Leu Thr Glu Glu
            275                 280                 285

Lys Lys Asp Lys Ala Ser Ile Arg Glu Phe Leu Leu Ala Glu Tyr Ser
            290                 295                 300

Phe Thr Ala Gly Tyr Asn Gly Phe Met Ser Ile Leu Trp Asp Thr Ser
305                 310                 315                 320

Lys Asn Thr Ala Gly Asp Met Asn Phe Tyr Asn Arg Glu Thr Asp Lys
            325                 330                 335

Trp Tyr Asp Glu Gln Ile Arg Asp Asn Phe Ile Asn Ile Ala Ala Gly
            340                 345                 350

Lys Phe Val Asp Pro Thr Lys Tyr Leu Val Asn Ser Asn Ser Glu Thr
            355                 360                 365

Ser Thr Lys Val Asp Ser Asp Gly Asn Val Gln Ile Asn Ile Gly Ser
    370                 375                 380

Lys Lys Val Asn Lys Val Ile Phe Asn Ala Lys Ile Ser Gly Ala Val
385                 390                 395                 400

Asn Ile Trp Asp Val Gly Phe Gly Val Ala Ser Ala Asp Lys Thr Gly
            405                 410                 415

Lys Trp Phe Gly Asp Pro Val Gly Gly Ala Glu Gly Val Lys Gln Asn
```

420                 425                 430
Asp Gly Thr Tyr Thr Phe Thr Val Asp Val Ser Ala Lys Asp Phe Asn
            435                 440                 445

Asp Tyr Val Gln Val Gln Arg Trp Trp Gly Asn Asp Asn Ile Thr Ile
    450                 455                 460

Asn Ser Val Thr Val Glu Phe Glu Gly Thr Ala Lys Arg Leu Asp Phe
465                 470                 475                 480

Asn Ala Tyr Lys Ala Ala Leu Lys
            485

<210> SEQ ID NO 4
<211> LENGTH: 1464
<212> TYPE: DNA
<213> ORGANISM: Epidinium ecaudatum
<220> FEATURE:
<223> OTHER INFORMATION: rumen anaerobic protozoan Epidinium ecaudatum
      cellulase family 5 protein (partial), Cel5AEec, cmc-06

<400> SEQUENCE: 4

```
aaaacggcga ttgaaaccgt gaacgatatg ggcctgggtt ggaacctggg caatacgttt      60
gactgcttcg gcacctggaa agaaattaaa acgccggatg accagatcac catgtggggc     120
aacgtggttc cgaccgaagc gatggtgacc acgatcaaaa aatacggtttt caaaacggtg    180 cgtttcccgg ttacctggat gaattttatg gatgaatctg gcaaagtgaa agcggaatgg    240
atggcccgcg ttaaagaagt cgtggattgg attgtgaaag caggcctgta ctgtatcctg    300
aacgttcatc acgacggcgt cagcggtaat tggctggcac agggtgctca tgtgaaagca    360
cgttatgtta cgctgtggac ccaaattgct accgaattta agattacga tgaccacctg     420 gtcttcgaat ccatgaacga agttgaatac aaaaacggta attcgttcga ttacaatagc    480
ctgctgaccc tgacgcaggc ctttgtcgat accgtgcgtg gctgggcgg taaaaactcg     540 gaccgcctgc tgctgatcag cggtatgaac acgaatctgg aaaacacctg tagcagcagc    600
tataaaatgc gacggataa agcaaacaaa ctggctatct ccatccatta ctacctgccg    660
ccgcagttta ccgttgaatc agataaaaat ccgtggaccct ggacggatga ccaaggcgtt   720
gtccacgaaa ttacccgct gcaaaaatgg ggcgatgagg gtaactacca agaaatggtg    780
acgaattttg aaaccatgaa aaaagcattc gtcgataaag gtattccggt gatcctgggc    840
gaagtgggtg ttctgacgga agagaaaaaa gacaaagcga gcattcgcga atttctgctg    900
gcagaatata gtttcaccgc tggctacaac ggttttatgt ccatcctgtg ggatacgtca    960
aaaaataccg cgggcgacat gaacttctat aatcgtgaaa ccgataaatg gtacgacgaa   1020
cagattcgcg ataacttcat taatatcgcg gcgggtaaat tgtggaccc gaccaaatat    1080 ctggttaact ccaattcaga aacctctacg aaagttgata gtgacggcaa cgtccaaatc    1140
aacatcggtt cgaaaaaagt taacaaagtc atcttcaatg cgaaaatcag cggcgccgtg    1200
aatatctggg atgtcggttt cggtgtggcg agcgccgata aaaccggcaa atggtttggt    1260
gacccggtgg gcggtgcaga aggcgttaaa cagaacgatg gcacctatac gttcaccgtg    1320
gatgtgtctg ccaaagattt taatgactac gttcaggtcc aacgttggtg gggcaacgat    1380
aatattacga tcaacagtgt gaccgttgaa tttgaaggca ccgcgaaacg cctggatttt    1440
aatgcctata aagcagctct gaaa                                            1464
```

<210> SEQ ID NO 5
<211> LENGTH: 352
<212> TYPE: PRT

<213> ORGANISM: Prevotella bryantii
<220> FEATURE:
<223> OTHER INFORMATION: Prevotella bryantii strain B14
      beta-1,4-endoglucanase (partial), Cel5APbr

<400> SEQUENCE: 5

| Ile | Asn | Gln | Asn | Ala | Thr | Tyr | Met | Glu | Glu | Ser | Ala | Gln | Ser | Ala | Val |
|---|---|---|---|---|---|---|---|---|---|---|---|---|---|---|---|
| 1 | | | | 5 | | | | | 10 | | | | | 15 | |

| Asp | Asn | Phe | Gly | Leu | Gly | Phe | Asn | Leu | Gly | Asn | Thr | Leu | Asp | Ala | Asn |
|---|---|---|---|---|---|---|---|---|---|---|---|---|---|---|---|
| | | | 20 | | | | | 25 | | | | | 30 | | |

| Gly | Cys | Gly | Thr | Gly | Lys | Pro | Val | Ala | Thr | Tyr | Glu | Thr | Phe | Trp | Gly |
|---|---|---|---|---|---|---|---|---|---|---|---|---|---|---|---|
| | | | 35 | | | | | 40 | | | | | 45 | | |

| Gln | Pro | Glu | Thr | Thr | Gln | Asp | Met | Met | Thr | Phe | Leu | Met | Gln | Asn | Gly |
|---|---|---|---|---|---|---|---|---|---|---|---|---|---|---|---|
| | 50 | | | | | 55 | | | | | 60 | | | | |

| Phe | Asn | Ala | Val | Arg | Ile | Pro | Val | Thr | Trp | Tyr | Glu | His | Met | Asp | Ala |
|---|---|---|---|---|---|---|---|---|---|---|---|---|---|---|---|
| 65 | | | | | 70 | | | | | 75 | | | | | 80 |

| Glu | Gly | Asn | Val | Asp | Glu | Ala | Trp | Met | Met | Arg | Val | Lys | Ala | Ile | Val |
|---|---|---|---|---|---|---|---|---|---|---|---|---|---|---|---|
| | | | | 85 | | | | | 90 | | | | | 95 | |

| Glu | Tyr | Ala | Met | Asn | Ala | Gly | Leu | Tyr | Ala | Ile | Val | Asn | Val | His | His |
|---|---|---|---|---|---|---|---|---|---|---|---|---|---|---|---|
| | | | 100 | | | | | 105 | | | | | 110 | | |

| Asp | Thr | Ala | Ala | Gly | Ser | Gly | Ala | Trp | Ile | Lys | Ala | Asp | Thr | Asp | Val |
|---|---|---|---|---|---|---|---|---|---|---|---|---|---|---|---|
| | | | 115 | | | | | 120 | | | | | 125 | | |

| Tyr | Ala | Ala | Thr | Lys | Glu | Lys | Phe | Lys | Lys | Leu | Trp | Thr | Gln | Ile | Ala |
|---|---|---|---|---|---|---|---|---|---|---|---|---|---|---|---|
| | 130 | | | | | 135 | | | | | 140 | | | | |

| Asn | Ala | Leu | Ala | Asp | Tyr | Asp | Gln | His | Leu | Leu | Phe | Glu | Gly | Tyr | Asn |
|---|---|---|---|---|---|---|---|---|---|---|---|---|---|---|---|
| 145 | | | | | 150 | | | | | 155 | | | | | 160 |

| Glu | Met | Leu | Asp | Gly | Asn | Asn | Ser | Trp | Asp | Glu | Pro | Gln | Lys | Ala | Ser |
|---|---|---|---|---|---|---|---|---|---|---|---|---|---|---|---|
| | | | | 165 | | | | | 170 | | | | | 175 | |

| Gly | Tyr | Glu | Ala | Leu | Asn | Asn | Tyr | Ala | Gln | Asp | Phe | Val | Asp | Ala | Val |
|---|---|---|---|---|---|---|---|---|---|---|---|---|---|---|---|
| | | | 180 | | | | | 185 | | | | | 190 | | |

| Arg | Ala | Thr | Gly | Gly | Asn | Asn | Ala | Thr | Arg | Asn | Leu | Ile | Val | Asn | Thr |
|---|---|---|---|---|---|---|---|---|---|---|---|---|---|---|---|
| | | | 195 | | | | | 200 | | | | | 205 | | |

| Tyr | Ala | Ala | Lys | Gly | Glu | Asn | Val | Leu | Asn | Asn | Phe | Met | Leu | Pro |
|---|---|---|---|---|---|---|---|---|---|---|---|---|---|---|
| | 210 | | | | | 215 | | | | | 220 | | | |

| Thr | Asp | Ala | Val | Asn | Asn | His | Leu | Ile | Val | Gln | Val | His | Ser | Tyr | Asp |
|---|---|---|---|---|---|---|---|---|---|---|---|---|---|---|---|
| 225 | | | | | 230 | | | | | 235 | | | | | 240 |

| Pro | Trp | Asn | Phe | Phe | Asn | Thr | Lys | Thr | Thr | Trp | Asp | Ser | Glu | Cys | His |
|---|---|---|---|---|---|---|---|---|---|---|---|---|---|---|---|
| | | | | 245 | | | | | 250 | | | | | 255 | |

| Asn | Thr | Leu | Thr | Glu | Ile | Phe | Ser | Ala | Leu | Ser | Lys | Lys | Phe | Thr | Thr |
|---|---|---|---|---|---|---|---|---|---|---|---|---|---|---|---|
| | | | 260 | | | | | 265 | | | | | 270 | | |

| Ile | Pro | Tyr | Ile | Ile | Gly | Glu | Tyr | Gly | Thr | His | Gly | Glu | Ser | Asp | Ile |
|---|---|---|---|---|---|---|---|---|---|---|---|---|---|---|---|
| | | | 275 | | | | | 280 | | | | | 285 | | |

| Ser | Val | Ser | Lys | Ser | Ser | Pro | Ala | Glu | Lys | Ile | Lys | Leu | Ala | Ala | Asp |
|---|---|---|---|---|---|---|---|---|---|---|---|---|---|---|---|
| | 290 | | | | | 295 | | | | | 300 | | | | |

| Gln | Ala | Ala | Asp | Met | Val | Lys | Leu | Ala | Lys | Asp | His | His | Ser | Ala | Thr |
|---|---|---|---|---|---|---|---|---|---|---|---|---|---|---|---|
| 305 | | | | | 310 | | | | | 315 | | | | | 320 |

| Phe | Tyr | Trp | Met | Ser | Ile | Phe | Asp | Gly | Ser | Asp | Arg | Ile | Gln | Pro | Gln |
|---|---|---|---|---|---|---|---|---|---|---|---|---|---|---|---|
| | | | | 325 | | | | | 330 | | | | | 335 | |

| Trp | Ser | Leu | Pro | Thr | Val | Val | Glu | Ala | Met | Gln | Glu | Ala | Tyr | Asn | Asn |
|---|---|---|---|---|---|---|---|---|---|---|---|---|---|---|---|
| | | | 340 | | | | | 345 | | | | | 350 | | |

<210> SEQ ID NO 6
<211> LENGTH: 1056
<212> TYPE: DNA
<213> ORGANISM: Prevotella bryantii
<220> FEATURE:

<223> OTHER INFORMATION: Prevotella bryantii strain B14
      beta-1,4-endoglucanase (partial), Cel5APbr

<400> SEQUENCE: 6

| | | | | | |
|---|---|---|---|---|---|
| attaaccaaa | atgcaaccta | catggaggag | agcgcgcaat | ccgcagtgga | caatttcggc | 60 |
| ctgggcttca | acctgggtaa | cactctggac | gcgaacggct | gcggcaccgg | caaaccggtg | 120 |
| gcgacctacg | agactttctg | gggtcaaccg | gagactaccc | aggacatgat | gaccttcctg | 180 |
| atgcagaacg | gtttcaacgc | ggttcgtatt | ccagtgacct | ggtacgaaca | catggacgcg | 240 |
| gaaggtaacg | tggacgaagc | gtggatgatg | cgcgtgaagg | cgattgttga | gtacgcgatg | 300 |
| aacgcgggcc | tgtacgcgat | tgttaacgtt | caccacgaca | ccgcggctgg | cagcggcgcg | 360 |
| tggatcaagg | ctgacaccga | cgtttacgcg | gcgaccaaag | aaaagtttaa | aaagctgtgg | 420 |
| acccaaatcg | ctaacgcgct | ggcggactac | gaccaacacc | tgctgttcga | gggctacaac | 480 |
| gaaatgctgg | acggcaacaa | cagctgggac | gagccgcaaa | aagcgagcgg | ttacgaagcg | 540 |
| ctgaataact | acgcgcaaga | cttcgttgac | gcggtgcgcg | ctaccggtgg | caacaacgcg | 600 |
| acccgcaatc | tgatcgttaa | cacctacgcc | gcagcgaagg | gtgagaacgt | tctgaacaat | 660 |
| ttcatgctgc | cgaccgacgc | ggttaacaat | caccctgatcg | ttcaggtgca | tagctacgac | 720 |
| ccgtggaact | tctttaacac | taagaccacc | tgggactccg | agtgccacaa | cactctgacc | 780 |
| gagatttta | gcgcgctgag | caagaaattt | accaccatcc | cgtacatcat | cggtgagtac | 840 |
| ggcacccacg | gtgaaagcga | catcagcgtt | agcaaaagca | gcccggctga | aaagatcaaa | 900 |
| ctggcggcgg | accaagcggc | ggacatggtt | aagctggcga | aggaccacca | cagcgcgacc | 960 |
| ttctattgga | tgtccatctt | tgacggtagc | gaccgcatcc | aaccgcaatg | gagcctgccg | 1020 |
| accgttgtgg | aagcgatgca | agaggcgtac | aacaac | | | 1056 |

<210> SEQ ID NO 7
<211> LENGTH: 482
<212> TYPE: PRT
<213> ORGANISM: Unknown
<220> FEATURE:
<223> OTHER INFORMATION: unidentified microorganism from rumen contents
      of a New Zealand dairy cow, bovine rumen microflora
<220> FEATURE:
<223> OTHER INFORMATION: cellulase, Cel5AUI

<400> SEQUENCE: 7

Ile Asn Val Leu Gln His His Pro Glu Val Glu Leu Ser Val Asp Lys
 1               5                  10                  15

Thr Ser Val Ser Phe Asn Arg Ser Gly Gly Glu Glu Thr Phe Thr Val
            20                  25                  30

Thr Ser Ser Thr Gln Pro His Val Ser Ala Asp Val Ser Trp Val Val
        35                  40                  45

Val Glu Thr Gly Lys Ile Asp Lys Asp His His Thr Glu Val Arg Val
    50                  55                  60

Leu Ala Gly Ala Asn Arg Lys Glu Ala Ser Ala Gly Thr Leu Thr Val
65                  70                  75                  80

Ser Cys Ser Asp Lys Lys Val Ser Val Ser Val Lys Gln Glu Ala Phe
                85                  90                  95

Val Ala Pro Ser Val Ala Ser Thr Thr Ala Val Thr Pro Gln Met Val
            100                 105                 110

Phe Asp Ala Met Gly Pro Gly Trp Asn Met Gly Asn His Met Asp Ala
        115                 120                 125

Ile Ser Asn Gly Val Ser Gly Glu Thr Val Trp Gly Asn Pro Lys Cys

```
                130                 135                 140
Thr Gln Ala Thr Met Asp Gly Val Lys Ala Gly Tyr Lys Ala Val
145                 150                 155                 160

Arg Ile Cys Thr Thr Trp Glu Gly His Ile Gly Ala Ala Pro Ala Tyr
                165                 170                 175

Ala Leu Glu Gln Lys Trp Leu Asp Arg Val Ala Glu Ile Val Gly Tyr
                180                 185                 190

Ala Glu Lys Ala Gly Leu Val Ala Ile Val Asn Thr His His Asp Glu
                195                 200                 205

Ser Tyr Trp Gln Asp Ile Ser Lys Cys Tyr Asn Asn Ala Ala Asn His
                210                 215                 220

Glu Lys Val Lys Asp Glu Val Phe Ser Val Trp Thr Gln Ile Ala Glu
225                 230                 235                 240

Lys Phe Lys Asp Lys Gly Glu Trp Leu Val Phe Glu Ser Phe Asn Glu
                245                 250                 255

Ile Gln Asp Gly Gly Trp Gly Trp Ser Asp Ala Phe Arg Lys Asn Pro
                260                 265                 270

Asp Ala Gln Tyr Lys Val Leu Asn Glu Trp Asn Gln Thr Phe Val Asp
                275                 280                 285

Ala Val Arg Ser Thr Gly Gly Gln Asn Ala Thr Arg Trp Leu Gly Ile
                290                 295                 300

Pro Gly Tyr Ala Cys Asn Pro Gly Phe Thr Ile Ala Gly Leu Val Leu
305                 310                 315                 320

Pro Lys Asp Tyr Thr Thr Ala Asn Arg Leu Met Val Ala Val His Asp
                325                 330                 335

Tyr Asp Pro Tyr Asp Tyr Thr Leu Lys Asp Pro Leu Ile Arg Gln Trp
                340                 345                 350

Gly His Thr Ala Asp Ala Asp Lys Arg Pro Ser Gly Asp Asn Glu Lys
                355                 360                 365

Ala Val Val Asp Val Phe Asn Asn Leu Lys Ala Ala Tyr Leu Asp Lys
                370                 375                 380

Gly Ile Pro Val Tyr Leu Gly Glu Met Gly Cys Ser Arg His Thr Ala
385                 390                 395                 400

Ala Asp Phe Pro Tyr Gln Lys Tyr Tyr Met Glu Tyr Phe Cys Lys Ala
                405                 410                 415

Ala Ala Asp Arg Leu Leu Pro Met Tyr Leu Trp Asp Asn Gly Ala Lys
                420                 425                 430

Gly Val Gly Ser Glu Arg His Ala Tyr Ile Asp His Gly Thr Gly Gln
                435                 440                 445

Phe Val Asp Glu Asp Ala Arg Thr Leu Val Gly Leu Met Val Lys Ala
                450                 455                 460

Val Thr Thr Lys Asp Ala Ser Tyr Thr Leu Glu Ser Val Tyr Asn Ser
465                 470                 475                 480

Ala Pro
```

<210> SEQ ID NO 8
<211> LENGTH: 1446
<212> TYPE: DNA
<213> ORGANISM: Unknown
<220> FEATURE:
<223> OTHER INFORMATION: unidentified microorganism from rumen contents
      of a New Zealand dairy cow, bovine rumen microflora
<220> FEATURE:
<223> OTHER INFORMATION: cellulase, Cel5AUI

<400> SEQUENCE: 8

```
attaacgtgc tgcaacatca cccggaagtc gaactgagcg tggataaaac gagtgtgtcc    60
tttaatcgtt ctggcggtga agaaaccttc acggttacca gctctaccca accgcatgtt   120
tcagcggatg tctcgtgggt ggttgtcgaa acgggcaaaa tcgataaaga ccatcacacc   180
gaagtccgtg tgctggccgg cgcaaaccgc aaagaagcga gcgcgggcac cctgaccgtg   240
tcatgctcgg ataaaaaagt tagcgtctct gtgaaacagg aagcctttgt ggcaccgagt   300
gttgcctcca ccacggcagt tacgccgcaa atggtcttcg acgcaatggg cccggggttgg  360
aacatgggca atcacatgga tgcgattagc aacggcgtgt ctggtgaaac cgtttggggt   420
aatccgaaat gcacgcaggc tacgatggat ggcgtcaaag cggcgggtta taaagccgtg   480
cgtatttgta ccacgtggga aggccacatc ggtgcagctc cggcctatgc actggaacag   540
aaatggctgg atcgcgtcgc cgaaattgtg ggctacgctg aaaaagcggg tctggtggca   600
atcgttaaca cccatcacga tgaatcatat tggcaagaca tctcgaaatg ctacaacaat   660
gcggccaatc atgaaaaagt gaaagacgaa gtctttagtg tgtggaccca gattgccgaa   720
aaattcaaag ataaaggcga atggctggtt tttgaaagtt caacgaaat ccaagatggc    780
ggttgggggtt ggtccgacgc ttttcgtaaa atccggatg cgcagtataa agtgctgaac   840
gaatggaatc aaaccttcgt tgatgctgtc cgtagcacgg gcggtcagaa cgcgacccgc   900
tggctgggca ttccgggtta tgcctgtaat ccgggcttta ccatcgcagg tctggttctg   960
ccgaaagatt ataccacggc taaccgcctg atggttgcgg tccatgatta cgacccgtat  1020
gattacacgc tgaaagaccc gctgattcgt cagtggggcc acaccgctga tgcggacaaa  1080
cgtccgtcag gtgacaatga aaaagcggtg gttgatgtgt tcaacaatct gaaagcagct  1140
tatctggaca aaggtatccc ggtttacctg ggcgaaatgg gttgctcgcg tcacaccgcg  1200
gcggatttcc cgtaccagaa atactacatg gaatacttct gtaaagcagc tgcggaccgc  1260
ctgctgccga tgtatctgtg ggataacggc gccaaaggcg tgggttcaga acgtcatgca  1320
tacattgacc acggcacggg tcaatttgtt gatgaagacg cccgcaccct ggtcggtctg  1380
atggtgaaag ccgttaccac gaaagatgca tcttataccc tggaaagtgt ttacaattcc  1440
gcgccg                                                              1446
```

<210> SEQ ID NO 9
<211> LENGTH: 312
<212> TYPE: PRT
<213> ORGANISM: Dictyoglomus turgidum
<220> FEATURE:
<223> OTHER INFORMATION: Dictyoglomus turgidum strain DSM 6724 glycoside hydrolase family 5, Cel5BDtu, locus Dtur_0670

<400> SEQUENCE: 9

```
Met Asn Asn Leu Pro Ile Lys Arg Gly Ile Asn Phe Gly Asp Ala Leu
  1               5                  10                  15

Glu Ala Pro Tyr Glu Gly Ala Trp Ser Gly Tyr Ile Ile Lys Asp Glu
             20                  25                  30

Tyr Phe Lys Ile Val Lys Asp Ala Gly Phe Asp His Val Arg Ile Pro
         35                  40                  45

Ile Lys Trp Ser Val Tyr Thr Gln Lys Glu Ala Pro Tyr Ser Ile Glu
     50                  55                  60

Lys Arg Ile Phe Asp Arg Val Asp His Leu Ile Glu Glu Gly Leu Lys
 65                  70                  75                  80

Asn Asn Leu His Val Ile Ile Asn Ile His His Tyr Glu Glu Ile Met
                 85                  90                  95
```

```
Glu Asp Pro Leu Gly Glu Lys Glu Arg Phe Leu Ala Ile Trp Arg Gln
                100                 105                 110

Ile Ser Glu His Tyr Lys Asp Tyr Pro Asn Asn Leu Tyr Phe Glu Leu
            115                 120                 125

Leu Asn Glu Pro Thr Gln Asn Leu Ser Ser Leu Trp Asn Gln Phe
        130                 135                 140

Leu Lys Glu Ala Ile Glu Val Ile Arg Arg Thr Asn Pro Glu Arg Lys
145                 150                 155                 160

Ile Ile Val Gly Pro Asp Asn Trp Asn Ser Leu Tyr Asn Leu Glu Lys
                165                 170                 175

Leu Ile Ile Pro Glu Asn Asp Glu Asn Ile Ile Ile Thr Phe His Tyr
            180                 185                 190

Tyr Asn Pro Phe Pro Phe Thr His Gln Gly Ala Gly Trp Val Lys Ile
        195                 200                 205

Asp Leu Pro Val Gly Val Lys Trp Leu Gly Thr Glu Glu Glu Lys Arg
    210                 215                 220

Glu Ile Glu Arg Glu Leu Asp Met Ala Val Ser Trp Ala Glu Glu His
225                 230                 235                 240

Gly Asn Ile Pro Leu Tyr Met Gly Glu Phe Gly Ala Tyr Ser Lys Ala
                245                 250                 255

Asp Met Glu Ser Arg Val Arg Trp Thr Asp Phe Val Ala Arg Ser Ala
            260                 265                 270

Glu Lys Arg Gly Ile Ala Trp Ser Tyr Trp Glu Phe Tyr Ser Gly Phe
        275                 280                 285

Gly Val Phe Asp Pro Glu Lys Asn Glu Trp Arg Thr Pro Leu Leu Arg
    290                 295                 300

Ala Leu Ile Pro Glu Arg Asn Ile
305                 310

<210> SEQ ID NO 10
<211> LENGTH: 936
<212> TYPE: DNA
<213> ORGANISM: Dictyoglomus turgidum
<220> FEATURE:
<223> OTHER INFORMATION: Dictyoglomus turgidum strain DSM 6724 glycoside
      hydrolase family 5, Cel5BDtu, locus Dtur_0670

<400> SEQUENCE: 10
atgaacaatc tgccgatcaa acgtggcatt aacttcggtg atgcgctgga agccccgtat     60
gaaggcgcgt ggagcggtta catcatcaaa gacgaatact tcaaaatcgt taaagatgcc    120
ggcttcgacc atgtccgcat cccgattaaa tggagcgtgt atacccagaa agaagcaccg    180
tactctatcg aaaaacgtat tttcgatcgc gtgaccatct gattgaaga aggcctgaaa     240 aacaacctgc acgttatcat caacatccat cactacgaag aaatcatgga agatccgctg    300
ggtgaaaaag aacgttttct ggcgatctgg cgccaaatta gcgaacacta taaagactac    360
ccgaacaatc tgtacttcga actgctgaac gaaccgaccc agaatctgag cagcgaactg    420
tggaaccaat ttctgaaaga agccatcgaa gttattcgtc gcacgaatcc ggaacgtaaa    480
attatcgtcg gtccggataa ctggaacagc ctgtataacc tggaaaaact gattatcccg    540
gaaaacgacg aaaacatcat catcaccttc cattactaca atccgttccc gttcacgcac    600
cagggtgcag gttgggtcaa aattgatctg ccggtgggcg ttaaatggct gggtacggaa    660
gaagaaaaac gtgaaatcga acgcgaactg gatatggccg tgagttgggc cgaagaacat    720
ggcaacattc cgctgtatat gggcgaattt ggtgcataca gtaaagctga tatggaatcc    780
```

```
cgtgtccgct ggaccgactt cgtggcacgt tccgctgaaa aacgcggtat tgcatggtca    840
tattgggaat tttactcggg ctttggtgtt ttcgatccgg agaaaaacga atggcgtacg    900
ccgctgctgc gcgctctgat cccggaacgc aatatt                             936
```

<210> SEQ ID NO 11
<211> LENGTH: 366
<212> TYPE: PRT
<213> ORGANISM: Clostridium thermocellum
<220> FEATURE:
<223> OTHER INFORMATION: endo-beta-1,4-glucanase (partial), Cel5CCth, celE

<400> SEQUENCE: 11

```
Ser Gly Thr Lys Leu Leu Asp Ala Ser Gly Asn Glu Leu Val Met Arg
  1               5                  10                  15

Gly Met Arg Asp Ile Ser Ala Ile Asp Leu Val Lys Glu Ile Lys Ile
                 20                  25                  30

Gly Trp Asn Leu Gly Asn Thr Leu Asp Ala Pro Thr Glu Thr Ala Trp
             35                  40                  45

Gly Asn Pro Arg Thr Thr Lys Ala Met Ile Glu Lys Val Arg Glu Met
 50                  55                  60

Gly Phe Asn Ala Val Arg Val Pro Val Thr Trp Asp Thr His Ile Gly
 65                  70                  75                  80

Pro Ala Pro Asp Tyr Lys Ile Asp Glu Ala Trp Leu Asn Arg Val Glu
                 85                  90                  95

Glu Val Val Asn Tyr Val Leu Asp Cys Gly Met Tyr Ala Ile Ile Asn
                100                 105                 110

Leu His His Asp Asn Thr Trp Ile Ile Pro Thr Tyr Ala Asn Glu Gln
            115                 120                 125

Arg Ser Lys Glu Lys Leu Val Lys Val Trp Glu Gln Ile Ala Thr Arg
130                 135                 140

Phe Lys Asp Tyr Asp Asp His Leu Leu Phe Glu Thr Met Asn Glu Pro
145                 150                 155                 160

Arg Glu Val Gly Ser Pro Met Glu Trp Met Gly Gly Thr Tyr Glu Asn
                165                 170                 175

Arg Asp Val Ile Asn Arg Phe Asn Leu Ala Val Val Asn Thr Ile Arg
                180                 185                 190

Ala Ser Gly Gly Asn Asn Asp Lys Arg Phe Ile Leu Val Pro Thr Asn
            195                 200                 205

Ala Ala Thr Gly Leu Asp Val Ala Leu Asn Asp Leu Val Ile Pro Asn
210                 215                 220

Asn Asp Ser Arg Val Ile Val Ser Ile His Ala Tyr Ser Pro Tyr Phe
225                 230                 235                 240

Phe Ala Met Asp Val Asn Gly Thr Ser Tyr Trp Gly Ser Asp Tyr Asp
                245                 250                 255

Lys Ala Ser Leu Thr Ser Glu Leu Asp Ala Ile Tyr Asn Arg Phe Val
            260                 265                 270

Lys Asn Gly Arg Ala Val Ile Ile Gly Glu Phe Gly Thr Ile Asp Lys
        275                 280                 285

Asn Asn Leu Ser Ser Arg Val Ala His Ala Glu His Tyr Ala Arg Glu
    290                 295                 300
```

```
Ala Val Ser Arg Gly Ile Ala Val Phe Trp Trp Asp Asn Gly Tyr Tyr
305                 310                 315                 320

Asn Pro Gly Asp Ala Glu Thr Tyr Ala Leu Leu Asn Arg Lys Thr Leu
                325                 330                 335

Ser Trp Tyr Tyr Pro Glu Ile Val Gln Ala Leu Met Arg Gly Ala Gly
                340                 345                 350

Val Glu Pro Leu Val Ser Pro Thr Pro Thr Pro Thr Leu Met
            355                 360                 365

<210> SEQ ID NO 12
<211> LENGTH: 1098
<212> TYPE: DNA
<213> ORGANISM: Clostridium thermocellum
<220> FEATURE:
<223> OTHER INFORMATION: endo-beta-1,4-glucanase (partial), Cel5CCth,
      celE

<400> SEQUENCE: 12
tccggcacca aactgctgga tgcgtcaggc aacgaactgg ttatgcgtgg tatgcgcgat       60
atttccgcca tcgacctggt caaagaaatt aaaatcggct ggaacctggg taatacccctg    120 gatgcaccga ccgaaacggc atggggtaac ccgcgtacca cgaaagcaat gattgaaaaa    180
gtgcgtgaaa tgggcttcaa tgctgttcgc gtcccggtga cctgggatac gcatattggt    240
ccggcaccgg attataaaat cgacgaagcg tggctgaacc gcgtcgaaga agtggttaat    300
tatgtgctgg attgcggcat gtacgcaatt atcaacctgc atcacgacaa tacctggatt    360
atcccgacgt atgctaacga acagcgtagc aaagaaaaac tggttaaagt ctgggaacaa    420
attgcaaccc gctttaaaga ttacgatgac cacctgctgt tcgaaacgat gaatgaaccg    480
cgtgaagtgg gctcgccgat ggaatggatg ggcggcacct atgaaaaccg tgatgttatt    540
aaccgcttta atctggcagt cgtgaatacg atccgtgcga gcggcggcaa caatgacaaa    600
cgcttcattc tggtcccgac caacgcagcc acgggtctgg atgtcgcact gaatgacctg    660
gtgatcccga acaatgatag ccgcgtgatt gtttctatcc atgcgtatag tccgtacttt    720
ttcgcgatgg atgtgaacgg cacctcatat tggggttcgg attacgacaa agcgagcctg    780
acctccgaac tggatgccat ctacaaccgt ttcgttaaaa atgccgcgc ggtcattatc       840 ggcgaatttg gcaccatcga taaaaacaat ctgagcagcc gtgtggcgca tgctgaacac    900
tatgcgcgtg aagccgtgtc tcgcggtatt gccgtgtttt ggtgggataa cggctattac    960
aatccgggtg acgcagaaac ctacgctctg ctgaatcgca aaacgctgtc atggtattac   1020
ccggaaatcg tgcaagcgct gatgcgtggt gctggcgtgg aaccgctggt gtctccgacc   1080
ccgaccccga ccctgatg                                                  1098
```

GLYCOSIDE HYDROLASES HAVING MULTIPLE HYDROLASE ACTIVITIES

CROSS-REFERENCE TO RELATED PATENT APPLICATIONS

The present application is the US National Stage of International Application No. PCT/US2012/036007, filed May 1, 2012, which claims benefit of priority to U.S. Provisional Patent Application No. 61/481,642, filed May 2, 2011; each application is incorporated by reference.

STATEMENT AS TO RIGHTS TO INVENTIONS MADE UNDER FEDERALLY SPONSORED RESEARCH AND DEVELOPMENT

The invention was made with government support under Contract Nos. DE-AC02-05CH11231 awarded by the U.S. Department of Energy. The government has certain rights in the invention.

REFERENCE TO A SEQUENCE LISTING SUBMITTED AS AN ASCII TEXT FILE

The Sequence Listing written in file SUBSEQTXT_77429-891656_009610US.txt, created on Oct. 31, 2013, 30,154 bytes, machine format IBM-PC, MS-Windows operating system, is hereby incorporated by reference in its entirety for all purposes.

BACKGROUND OF THE INVENTION

One major challenge in development of biofuels is to efficiently convert lignocellulosic biomass into fermentable sugars for the production of biofuels and commodity chemicals. Lignocellulosic biomass contain cellulose, hemicellulose (xylan and mannan) and lignin. Hydrolyzing the first two components needs the combination of cellulases, xylanases and mannanases, which are expensive for industrial processes. Currently, industrial processes rely on enzyme cocktails to hydrolyze lignocellulosic biomass, which contain cellulases and hemicellulases (xylanases and mannanases, etc.) from fungi.

BRIEF SUMMARY OF THE INVENTION

The present invention provides for recombinant glycoside hydrolases, optionally isolated, having at least two activities selected from the group consisting of cellulase activity, xylanase activity, and mannanase activity, wherein the glycoside hydrolase comprises the following amino acids (corresponding to positions in SEQ ID NO:1):
  asparagine (N), aspartic acid (D), glutamine (Q) or glutamic acid (E) at position 20, aspartic acid (D) or glutamic acid (E) at position 23,
  proline (P) at position 53,
  histidine (H) at position 95,
  histidine (H) at position 96 and
  aspartic acid (D) or glutamic acid (E) at position 287,
wherein the recombinant glycoside hydrolase has an increased cellulase activity, xylanase activity, and/or mannanase activity compared to the glycoside hydrolase of SEQ ID NO:1.

In some embodiments, the recombinant glycoside hydrolase is a GH5 glycoside hydrolase.

In some embodiments, the recombinant glycoside hydrolase has a cellulase activity, xylanase activity, and/or mannanase activity at least 10% higher than the activity of glycoside hydrolase of SEQ ID NO:1.

In some embodiments, the hydrolase has cellulase activity, xylanase activity, and mannanase activity.

In some embodiments, the recombinant glycoside hydrolase comprises at least one amino acid substitution compared to a naturally-occurring glycoside hydrolase at at least one amino acid position corresponding to positions 20, 23, 53, 95, 96, or 287 of SEQ ID NO:1.

In some embodiments, the recombinant glycoside hydrolase comprises an amino acid sequence substantially (e.g., at least 60%, 70%, 80%, 85%, 90%, or 95%) identical to any of SEQ ID NOs: 3, 5, 7, 9, or 11.

The present invention also provides for isolated nucleic acids comprising a polynucleotide encoding a glycoside hydrolase having at least two activities selected from the group consisting of cellulase activity, xylanase activity, and mannanase activity, wherein the glycoside hydrolase comprises the following amino acids (corresponding to positions in SEQ ID NO:1): asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, wherein the recombinant glycoside hydrolase has an increased cellulase activity, xylanase activity, and/or mannanase activity compared to the glycoside hydrolase of SEQ ID NO:1, and optionally as otherwise described above.

The present invention also provides for an expression vector comprising an expression cassette, the expression cassette comprising a heterologous promoter operably linked to a polynucleotide encoding a glycoside hydrolase having at least two activities selected from the group consisting of cellulase activity, xylanase activity, and mannanase activity, wherein the glycoside hydrolase comprises the following amino acids (corresponding to positions in SEQ ID NO:1): asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, wherein the recombinant glycoside hydrolase has an increased cellulase activity, xylanase activity, and/or mannanase activity compared to the glycoside hydrolase of SEQ ID NO:1, and optionally as otherwise described above.

The present invention also provides for a cell culture comprising cells that comprise an expression cassette, the expression cassette comprising a heterologous promoter operably linked to a polynucleotide encoding a glycoside hydrolase having at least two activities selected from the group consisting of cellulase activity, xylanase activity, and mannanase activity, wherein the glycoside hydrolase comprises the following amino acids (corresponding to positions in SEQ ID NO:1): asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, wherein the recombinant glycoside hydrolase has an increased cellulase activity, xylanase activity, and/or mannanase activity compared to the glycoside hydrolase of SEQ ID NO:1, and optionally as otherwise described above.

The present invention also provides for methods of generating free sugars from a mixture comprising at least two polymeric substrates selected from the group consisting of cellulose, xylan and mannan. In some embodiments, the method comprises contacting the mixture with a glycoside hydrolase under conditions such that the glycoside hydrolase hydrolyzes the at least two polymeric substrates, wherein the glycoside hydrolase comprises the following amino acids (corresponding to positions in SEQ ID NO:1): asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, thereby generating free sugars.

In some embodiments, the glycoside hydrolase is a recombinant glycoside hydrolase.

In some embodiments, the recombinant glycoside hydrolase is a GH5 glycoside hydrolase.

In some embodiments, the glycoside hydrolase has an increased cellulase activity, xylanase activity, and/or mannanase activity compared to the glycoside hydrolase of SEQ ID NO:1.

In some embodiments, the mixture comprises cellulose, xylan and mannan and the glycoside hydrolase hydrolyzes each of the cellulose, xylan and mannan.

In some embodiments, the glycoside hydrolase comprises at least one amino acid substitution compared to a naturally-occurring glycoside hydrolase at at least one amino acid position corresponding to positions 20, 23, 53, 95, 96, or 287 of SEQ ID NO:1.

In some embodiments, the glycoside hydrolase comprises an amino acid sequence substantially (e.g., at least 60%, 70%, 80%, 85%, 90%, or 95%) identical to any of SEQ ID NOs: 3, 5, 7, 9, or 11.

The present invention also provides for a method of generating a polynucleotide encoding a mutated glycoside hydrolase with activity to hydrolyze at least two polymeric substrates selected from the group consisting of cellulose, xylan and mannan. In some embodiments, the method comprises: introducing at least one nucleotide change to a coding region of a polynucleotide encoding a native glycoside hydrolase, resulting in at least one amino acid change in the glycoside hydrolase to generate a mutated polynucleotide encoding a mutated glycoside hydrolase, wherein the introducing changes at least one amino acid at positions 20, 23, 53, 95, 96, or 287 (corresponding to positions in SEQ ID NO:1) of the native glycoside hydrolase such that the mutated glycoside hydrolase comprises each of the following amino acids (corresponding to positions in SEQ ID NO:1): asparagine or aspartic acid at position 20, aspartic acid or glutamate at position 23, proline at position 53, histidine at position 95, histidine at position 96 and aspartate or glutamate at position 287, wherein the mutated glycoside hydrolase has an increased cellulase activity, xylanase activity, and/or mannanase activity compared to the native glycoside hydrolase.

In some embodiments, the glycoside hydrolase is a GH5 glycoside hydrolase.

In some embodiments, the method further comprises translating and purifying the mutated glycoside hydrolase.

In some embodiments, the mutated glycoside hydrolase has an increased cellulase activity, xylanase activity, and mannanase activity compared to the native glycoside hydrolase.

In some embodiments, the mutated glycoside hydrolase comprises an amino acid sequence substantially (e.g., at least 60%, 70%, 80%, 85%, 90%, or 95%) identical to any of SEQ ID NOs: 3, 5, 7, 9, or 11.

DEFINITIONS

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methyl-phosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156).

A "promoter" is defined as an array of nucleic acid control sequences that direct transcription of an operably linked nucleic acid. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A polynucleotide sequence is "heterologous to" an organism or a second polynucleotide sequence if it originates from a foreign species, or, if from the same species, is modified from its original form. For example, a heterologous promoter operably linked to a coding sequence refers to a coding sequence from a species different from that from which the promoter was derived, or, if from the same species, a coding sequence which is different from any naturally occurring allelic variants.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases or polymerases, in a form not found in nature. Thus an isolated, mutant glycoside hydrolase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

The phrase "host cell" refers to a cell from any organism. Exemplary host cells are derived from plants, bacteria, yeast, fungi, insects or animals, including humans. Methods for introducing polynucleotide sequences into various types of host cells are well known in the art. Host cells can be isolated from an organism rather than as part of an organism.

An "expression cassette" refers to a nucleic acid construct, which when introduced into a host cell, results in transcription and/or translation of an RNA or polypeptide, respectively.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Exemplary expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "isolated" or "biologically pure" refer to material that is substantially or essentially free of components that normally accompany it in its native state.

"Correspondence" of one amino acid sequence to another sequence (e.g., to SEQ ID NO:1) is based on the convention of numbering according to amino acid position number of one sequence (in this case, SEQ ID NO:1) and then aligning the sequences in a manner that maximizes the percentage of sequence identity. Because not all positions within a given "corresponding region" need be identical, non-matching positions within a corresponding region may be regarded as "corresponding positions." Accordingly, an amino acid "corresponding to position [X] of SEQ ID NO:1" refers to an amino acid in a polypeptide of interest that aligns with the equivalent amino acid of SEQ ID NO:1. Generally, as described herein, the amino acid corresponding to a position of a glycoside hydrolase polypeptide can be determined using an alignment algorithm such as BLAST as described herein. "Correspondence" is with reference to positions in SEQ ID NO:1 and thus a "corresponding" position of an amino acid in another (test) glycoside hydrolase may have a different numerical position in the test glycoside hydrolase. For example, the aspartic acid (D) at position 14 of SEQ ID NO:9 corresponds to position 20 of SEQ ID NO:1.

The phrase "substantially identical," in the context of two nucleic acids or polypeptides, refers to a sequence or subsequence that has at least 40% sequence identity with a reference sequence. Alternatively, percent identity can be any integer from 40% to 100%. Additional embodiments include at least: 40%, 45%, 50%, 55%, 60%, 65%, 70%, 75%, 80%, 85%, 90%, 95%, or 99% compared to a reference sequence using the programs described herein; preferably BLAST using standard parameters, as described below. The present invention provides sequences substantially identical to SEQ ID NOS:1, 2, 3, 4, 5, 6, 7, 8, 9, 10, 11 and containing the specified amino acids (or for nucleic acid sequences, encoding those amino acids) at positions corresponding to SEQ ID NO:1 as follows: asparagine (N), aspartate (D), glutamine (Q) or glutamic acid (E) at position 20, aspartate (D) or glutamic acid (E) at position 23, proline (P) at position 53, histidine (H) at position 95, histidine (H) and position 96 and aspartic acid (D) or glutamic acid (E) at position 287.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. If no range is provided, the comparison window is the entire length of the reference sequence. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word-length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions.

"Glycoside hydrolase" refers to an enzyme that catalyzes the hydrolysis of the glycosidic linkage to release smaller sugars.

A "cellulase" is a glycoside hydrolase enzyme that hydrolyzes cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). Endoglucanases act mainly on the amorphous parts of the cellulose fiber, whereas cellobiohydrolases are also able to degrade crystalline cellulose.

A "xylanase" is a glycoside hydrolase enzyme that catalyzes the endo-hydrolysis of 1,4-beta-D-xylosidic linkages in xylans. Xylanases include enzymes classified as a 1,4-beta-D-xylan-xylohydrolase (E.C. 3.2.1.8). Xylanase activity can be determined, for example, using birchwood xylan as substrate. One unit of xylanase activity is defined as 1.0 mmole of reducing sugar (measured in glucose equivalents as described by Lever, 1972, A new reaction for colorimetric determination of carbohydrates, Anal. Biochem 47: 273-279) produced per minute during the initial period of hydrolysis at 50.degree. C., pH 5 from 2 g of birchwood xylan per liter as substrate in 50 mM sodium acetate pH 5 containing 0.01% TWEEN® 20.

A mannanase is a glycoside hydrolase that hydrolyzes 1,4-β-D-mannosidic linkages in mannans, galactomannans and/or glucomannans. "Mannanase activity" refers to hydrolysis of 1,4-β-D-mannosidic linkages in mannans, galactomannans and/or glucomannans. Mannases include enzymes classified as EC 3.2.1.78.

An "increase" in enzymatic activity can be any measurable increase compared to a control. Where a mutated enzyme's activity is tested, the increase is measured compared to a control enzyme, which is the parent enzyme from which the mutant was derived. In some embodiments, the increased activity of the enzymes described herein, is at least, e.g., 5%, 10%, 20%, 50%, 100%, 200% or more of the control enzyme activity. In some embodiments, a mutated enzyme can show an increase in one activity (e.g., cellulase activity) but not an increase in a second activity (e.g., mannanase activity). In some embodiments, the mutated enzyme has an increase in two or more activities (e.g., cellulase and mannanase activity, cellulase and xylanase activity, or mannanase and xylanase activity) compared to a control enzyme. In some embodiments, a mutated enzyme of the invention has an increase in three activities (i.e., cellulase, mannanase, and xylanase activity) compared to a control enzyme.

A "naturally-occurring" glycoside hydrolase refers to a glycoside hydrolase having the same amino acid sequence as a glycoside hydrolase expressed in a cell that has not been recombinantly modified or mutated by human effort. In some embodiments, a recombinant glycoside hydrolase of the invention comprises a polypeptide sequence identical to a naturally-occurring glycoside hydrolase except that the recombinant glycoside hydrolase has one or more (e.g., 1, 2, 3, 4, 5) amino acid substitution(s) at positions corresponding to SEQ ID NO:1 as follows: asparagine (N), aspartate (D), glutamine (Q) or glutamic acid (E) at position 20, aspartate (D) or glutamic acid (E) at position 23, proline (P) at position 53, histidine (H) at position 95, histidine (H) and position 96 and aspartic acid (D) or glutamic acid (E) at position 287, i.e., such that the variant differs at at least one of position 20, 23, 53, 95, 96, and/or 287 of the naturally-occurring glycoside hydrolase.

"Free sugars," in the context of this invention, refer to monomeric sugars or sugars that are otherwise fermentable.

The term "native," in the context of glycoside hydrolase mutagenesis, refers to a glycoside hydrolase that is to be mutated, e.g., to introduce one or more amino acid change such that the enzyme becomes more promiscuous in substrate use, e.g., by introduction of one or more of: asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287 (corresponding to positions in SEQ ID NO:1). The term "native" should not be confused with "naturally-occurring." In the context of this application, a "native" enzyme can be a naturally-occurring or recombinant or other type of enzyme, and the term is simply used to refer to the enzyme before improvement according to the present invention.

DETAILED DESCRIPTION

I. Introduction

Figure 1A:
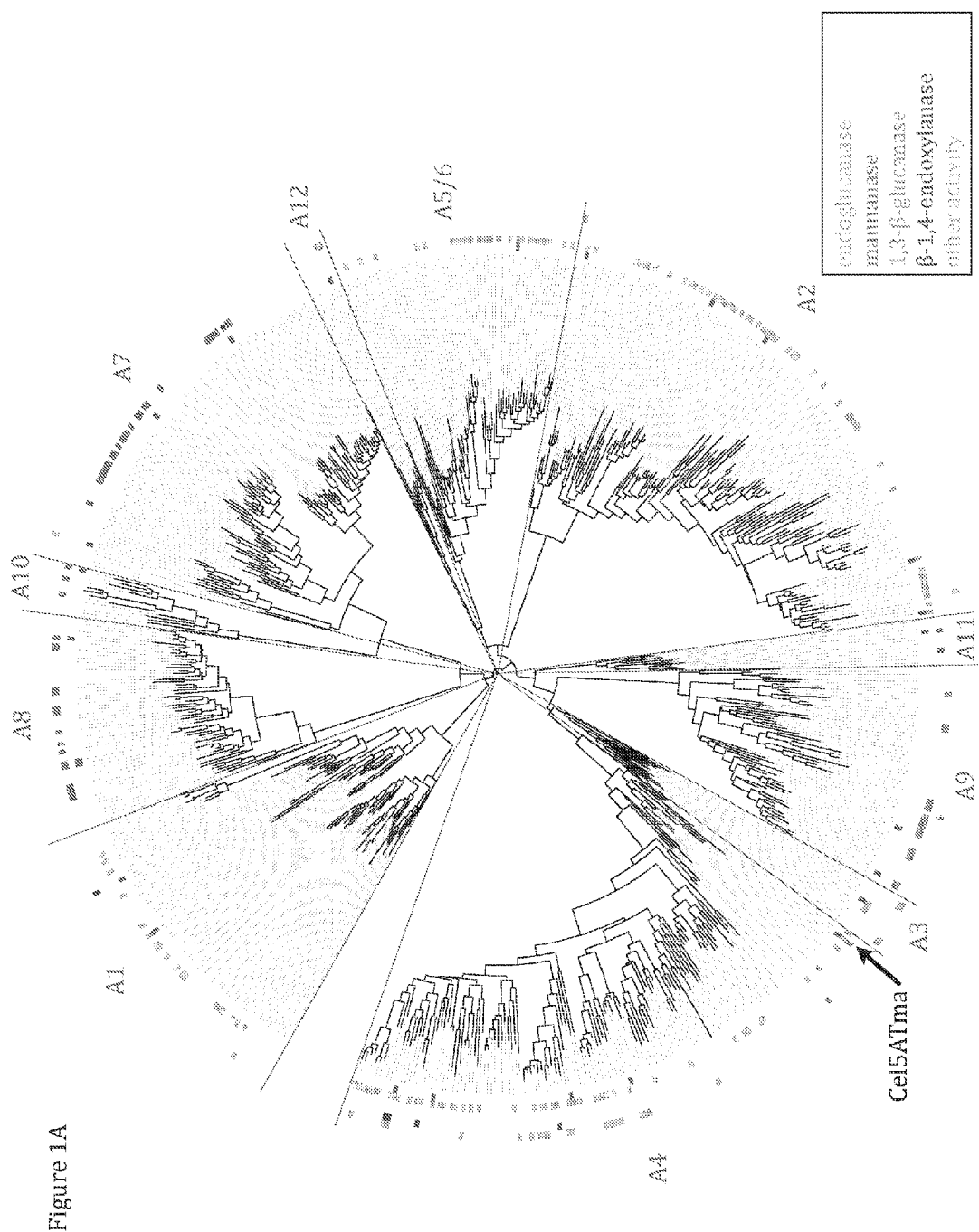
FIG. 1: (A) A phylogenetic tree of the GH5 family constructed from a structure-based sequence alignment. Experimental characterizations from the Carbohydrate-Active Enzymes database (CAZy) are depicted in the outer rings for endoglucanases, mannanases, 1,3-β-glucosidases, licheninases and other functions. Genes with structures are represented by grey boxes. Subfamilies A1-A10 are labeled. (B) The structure of active site residues from the structure of Cel5ATma (PDB id 3MMW, chain A) with the modeled pose of cellotriose from Perreira, et al.

Structure and sequence information was analyzed to build a high-resolution multiple sequence alignment for glycoside hydrolase family 5 (GH5). This alignment enabled prediction of a sequence pattern responsible for broad substrate specificity exhibited in some subfamilies of GH5. This pattern was identified by comparing amino acid distributions at active site residues and quantitatively identifying positions that differed significantly between GH5 subfamily A4 and GH5 mannanase subfamilies. The amino acid pattern conferring dual-specificity for endoglucananse and mannanase activities in GH5-A4 is: asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287. This numbering is based of the alignment to Cel5ATma (SEQ ID NO:1).

We experimentally confirmed that this pattern determined substrate specificity in one GH5 enzyme experimentally and also demonstrated that this substrate specificity pattern is used by other bifunctional enzymes in GH5-A4 subfamily. We then applied this knowledge to improve the cellulase and mannanase activities of one GH5-A4 enzyme by 30% and 300%, respectively.

Accordingly, the present invention provides for methods for making glycoside hydrolases with increased activity in at least two, and some embodiments, all three of the following activities: cellulose activity, mannanase activity, and xylanase activity. The invention also provides for glycoside hydrolases having increased activity in at least two, or in some embodiments, all three, of the activities. The present invention thus allows for use of biocatalysts with multiple functions that will reduce the enzyme loading so as to reduce the costs. For example, glycoside hydrolases with cellulase, mannanase and xylanase activities reduce the cost of multiple enzymes. Additionally, these multi-functional enzymes could eliminate the substrate competition effects which could greatly improve the efficiency of the whole hydrolysis process.

The invention allows people to use these multi-functional glycoside hydrolases for the saccharification of lignocellulosic biomass, which would significantly reduce enzyme loading and eliminate substrate competition effects. Therefore the invention could greatly increase the efficiency and lower the costs of this process. Additionally, the invention allows introduction of new glycoside hydrolase activities— such as cellulase, mannanase and xylanase activities—into existing enzymes and improves the performance of enzymes already containing these activities.

This invention can be used in the hydrolysis of pretreated biomass for the production of sugars from biomass in either a single step pretreatment and saccharification reaction or in separate step for the hydrolysis of cellulose and hemicellulose polymers to simpler sugars. The resulting sugars can be used in all processes that use C6 and C5 sugars like glucose, mannose and xylose as the starting materials. The process would be of significant interest in biomass processing or biofuels and other biomaterials, paper recycling and pulp processing for paper manufacturing. This invention could also be used for any industrial, research and educational facilities to engineer multi-functional glycoside hydrolases and improve the corresponding enzyme activities.

II. Introduction of Amino Acid Changes Conferring Increased Enzymatic Activity

In some embodiments, the present invention relates to methods for obtaining a variant (e.g., a mutant) glycoside hydrolase having increased activity in at least two, and some embodiments, all three of the following activities: cellulose activity, mannanase activity, and xylanase activity. Generally, it is believed that any glycoside hydrolase can be mutated to improve substrate use by mutating the glycoside hydrolase amino acid sequence to comprise: asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, where the positions correspond to those in SEQ ID NO:1.

In some embodiments, the glycoside hydrolase is a GH5 glycoside hydrolase. See, e.g., Henrissat B, et al. *Proc Natl Acad Sci USA* 93(11) 5674 (1996); Henrissat B, et al. *Proc Natl Acad Sci USA* 92(15) 7090-7094 (1995); Jenkins J, et al. *FEBS Lett* 362(3) 281-5 (1995). In some embodiments, the GH5 glycoside hydrolase is from one of the sub families selected from A1, A2, A3, A4, A5, A6, A7, A8, A9, A10, A11, or A12. In some embodiments, the glycoside hydrolase variant is a glycoside hydrolase selected from FIG. 5, wherein the hydrolase has been mutated to comprise: asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287, where the positions correspond to those in SEQ ID NO:1.

In some embodiments, the invention provides for a method of generating a variant (e.g., a mutant) glycoside hydrolase having increased activity in at least two, and some embodiments, all three of the following activities: cellulose activity, mannanase activity, and xylanase activity comprising: (a) introducing into a parent (i.e., a "native") glycoside hydrolase a substitution at one or more (several) positions corresponding to positions 20, 23, 53, 95, 96, 287 corresponding to SEQ ID NO:1, wherein the variant has increased activity in at least two, and some embodiments, all three of the following activities: cellulose activity, mannanase activity, and xylanase activity; and (b) recovering the variant. In some embodiments, the glycoside hydrolase variant has at least 10%, 20%, 30%, 50%, 100%, 150%, 200%, 300% or more xylanase activity than the parent (e.g., native enzyme). In some embodiments, the glycoside hydrolase variant has at least 10%, 20%, 30%, 50%, 100%, 150%, 200%, 300% or more cellulase activity than the parent (e.g., native enzyme). In some embodiments, the glycoside hydrolase variant has at least 10%, 20%, 30%, 50%, 100%, 150%, 200%, 300% or more mannanase activity than the parent (e.g., native enzyme).

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

III. Glycoside Hydrolase Variants

The present invention provides for glycoside hydrolase variants having at least two activities selected from the group consisting of cellulase activity, xylanase activity, and mannanase activity, wherein the glycoside hydrolase comprises the following amino acids (corresponding to positions in SEQ ID NO:1): asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287.

In some embodiments, the glycoside hydrolase variant has an increased cellulase activity, xylanase activity, and/or mannanase activity compared to the glycoside hydrolase of SEQ ID NO:1 or of an otherwise identical naturally-occurring or native glycoside hydrolase but not having at least one of: asparagine (N), aspartic acid (D), glutamine (Q) or glutamic acid (E) at position 20, aspartic acid (D) or glutamic acid (E) at position 23, proline (P) at position 53, histidine (H) at position 95, histidine (H) and position 96 and aspartic acid (D) or glutamic acid (E) at position 287 corresponding to SEQ ID NO:1.

In some embodiments, the glycoside hydrolase variant is a GH5 glycoside hydrolase. In some embodiments, the GH5 glycoside hydrolase is from one of the sub families selected from A1, A2, A3, A4, A5, A6, A7, A8, A9, A10, A11, or A12.

The glycoside hydrolase variants can be purified and/or isolated as desired. In some embodiments, the glycoside hydrolase variant are recombinant glycoside hydrolases.

IV. Nucleic Acid Constructs

The present invention also relates to nucleic acid constructs comprising a nucleotide sequence encoding a glycoside hydrolase variant of the present invention operably linked to one or more control sequences which direct the expression of the coding sequence in a suitable host cell under conditions compatible with the control sequences. Expression will be understood to include any step involved in the production of the variant including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of a variant of the present invention. The term "coding sequence" is defined herein as a nucleotide sequence which directly specifies the amino acid sequence of its protein product. The boundaries of a genomic coding sequence are generally determined by the ATG start codon, or alternative start codons such as GTG and TTG, located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleotide sequences.

In isolated nucleotide sequence encoding a glycoside hydrolase variant of the present invention may be manipulated in a variety of ways to provide for expression of the variant. Manipulation of the nucleotide sequence prior to its insertion into a vector may be desirable or necessary depending on the expression vector. The techniques for modifying nucleotide sequences utilizing recombinant DNA methods are well known in the art.

The term "control sequences" is defined herein to include all components which are necessary or advantageous for the expression of a glycoside hydrolase variant of the present invention. Each control sequence may be native or foreign to the nucleotide sequence encoding the variant. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a variant glycoside hydrolase of the present invention.

The control sequence may be an appropriate promoter sequence, which is recognized by a host cell for expression of the nucleotide sequence. The promoter sequence contains transcriptional control sequences which mediate the expression of the variant glycoside hydrolase. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

The glycoside hydrolases of the invention can be expressed in any host cell, as desired. Exemplary cell types include, e.g., bacterial, fungal, insect, mammalian, and plant cells. In view of different codon usage of different types of cells, it will be appreciated that codon optimization of the coding sequence can be used to enable or improve expression in a particular cell type. The invention provides for cell cultures for expressing the glycoside hydrolases of the invention.

The present invention also relates to recombinant expression vectors comprising a nucleotide sequence encoding a variant glycoside hydrolase of the present invention, a promoter, and transcriptional and translational stop signals. The various nucleotide and control sequences described above may be joined together to produce a recombinant expression vector which may include one or more convenient restriction sites to allow for insertion or substitution of the nucleotide sequence encoding the variant at such sites. Alternatively, the nucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

The vector may be an autonomously replicating vector, i.e., a vector which exists as an extrachromosomal entity, the replication of which is distinct from chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention optionally contain an element(s) that permits integration of the vector into the host cell's genome or autonomous replication of the vector in the cell independent of the genome.

V. Methods of Production

The present invention also relates to methods for producing a glycoside hydrolase variant, comprising: (a) cultivating a host cell under conditions suitable for the expression of the variant, wherein the host cell comprises a nucleotide sequence which has been modified to encode the variant comprising a substitution at one or more positions corresponding to positions to positions 20, 23, 53, 95, 96, 287 of SEQ ID NO:1, as described herein; and (b) recovering the variant from the cultivation medium.

In some production methods of the present invention, the host cells are cultivated in a nutrient medium suitable for production of the glycoside hydrolase variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

In an alternative embodiment, the glycoside hydrolase variant is not recovered, but rather a host cell of the present invention expressing a variant is used as a source of the variant.

The glycoside hydrolase variant may be detected using methods known in the art that are specific for the polypeptides. These detection methods may include use of specific antibodies, formation of ari enzyme product, or disappearance of an enzyme substrate. For example, an enzyme assay may be used to determine the activity of the polypeptide as described herein in the Examples.

The resulting glycoside hydrolase variant may be recovered by methods known in the art. For example, the polypeptide may be recovered from the nutrient medium by conventional procedures including, but not limited to, collection, centrifugation, filtration, extraction, spray-drying, evaporation, or precipitation.

A glycoside hydrolase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure glycoside hydrolase variants.

VI. Degradation of Biomass to Monosaccharides, Disaccharides, and Polysaccharides The glycoside hydrolase variants, polypeptides having glycoside hydrolase activity, and host cells of the present invention may be used in the production of monosaccharides, disaccharides, and polysaccharides as chemical or fermentation feedstocks from biomass for the production of ethanol, plastics, or other products or intermediates. The glycoside variants and polypeptides having glycoside hydrolase activity may be in the form of a crude fermentation broth with or without the cells removed or in the form of a semi-purified or purified enzyme preparation. Alternatively, a host cell of the present invention may be used as a source of the variant or polypeptide having glycoside hydrolase activity in a fermentation process with the biomass. Biomass can include, but is not limited to, wood resources, municipal solid waste, wastepaper, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). Other examples of biomass include, without limitation, crops such as starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes, or wood), process waste, and paper sludge; and aquatic plants such as algae, water weeds, water hyacinths, or reeds and rushes. Other examples of biomass include sorghum, rice hulls, rice straw, wheat straw, and other straws.

In some embodiments, the glycoside hydrolase variants of the invention are used to hydrolyze two or more polymeric substrates in a mixture, wherein the substrates are selected from the group consisting of cellulose, xylan and mannan, thereby hydrolyzing the two or more substrates to produce free sugars. In some embodiments, the two sugars are at least cellulose and xylan. In some embodiments, the two sugars are at least xylan and mannan. In some embodiments, the two sugars are at least cellulose and mannan. In some embodiments, all three of cellulose, xylan and mannan are hydrolyzed by the glycoside hydrolase variant.

In some embodiments, the predominant polysaccharide in the primary cell wall of biomass is cellulose, the second most abundant is hemi-cellulose, and the third is pectin. The secondary plant cell wall, produced after the cell has stopped growing, also contains polysaccharides and is strengthened through polymeric lignin covalently cross-linked to hemi-cellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Although in many embodiments it is envisioned that combinations are not required, in some embodiments, the glycoside hydrolase variants and polypeptides having glycoside hydrolase activity of the present invention may be used in conjunction with other enzymes (e.g., endo-1,4-beta-glucanases or 1,4-beta-D-glucan-4-glucanohydrolases (EC 3.2.1.4), which act randomly on soluble and insoluble 1,4- beta-glucan substrates; exo-1,4-beta-D-glucanases, e.g., the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans; and beta-D-glucosidases or beta-D-glucoside glucohydrolases (EC 3.2.1.21), which act to release D-glucose units from cellobiose and soluble cellodextrins, as well as an array of glycosides) enzymes to further degrade the cellulose component of the biomass substrate, (see, for example, Brigham et al., 1995, in Handbook on Bioethanol (Charles E. Wyman, editor), pp. 119-141, Taylor & Francis, Washington D.C.; Lee, 1997, Journal of Biotechnology 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

VII. Other Uses

The glycoside hydrolase variants or polypeptides having glycoside hydrolase activity of the present invention may also be used in the treatment of textiles as biopolishing agents and for reducing fuzz, pilling, texture modification, and stonewashing (N. K. Lange, in P. Suominen, T. Reinikainen (Eds.), *Trichoderma reesei* Cellulases and Other Hydrolases, Foundation for Biotechnical and Industrial Fermentation research, Helsinki, 1993, pp. 263-272). In addition, the described variants or polypeptides having glycoside hydrolase activity may also be used in wood processing for biopulping or debarking, paper manufacturing for fiber modification, bleaching, and reduction of refining energy costs, whitewater treatment, important to wastewater recycling, lignocellulosic fiber recycling such as deinking and secondary fiber processing, and wood residue utilization (S. D, Mansfield and A. R. Esteghlalian in S. D, Mansfield and J. N. Saddler (Eds.), Applications of Enzymes to Lignocellulosics, ACS Symposium Series 855, Washington, D.C., 2003, pp. 2-29).

EXAMPLES

The following examples are offered to illustrate, but not to limit the claimed invention.

Results

Diversity of Functions in the GH5 Family

The glycosyl hydrolase 5 (GH5) family contains a large diversity of functions, including beta-1,4-endoglucanases (endoglucanase; EC number 3.2.1.4), beta-1,4-mannanases (mannanases; EC number 3.2.1.78), beta-1,3-glucanases (3.2.1.6), licheninases (3.2.1.73), beta-1,4-xylanase (3.2.1.8) and others, and many genes with sequence identity to each other below 10%. To build a high-quality sequence alignment for this diverse family we used sequence information to align nearby sequences and combined these with structural information. For each of 23 GH5 structures with less than 90% sequence identity to one another, we used BLAST against GH5 sequences from CAZy to find sequences within 25-90% sequence identity. These BLASTed sequences were built into alignments with MUSCLE to form sub-alignments. Then we used 3dhit to pairwise structurally align each structure to the Cel5ATma structure (PDB id 3MMW, chain A), and used the structural alignments to combine the sequence subalignments for each structure into one large sequence alignment (see Methods for details).

Figure 1B:
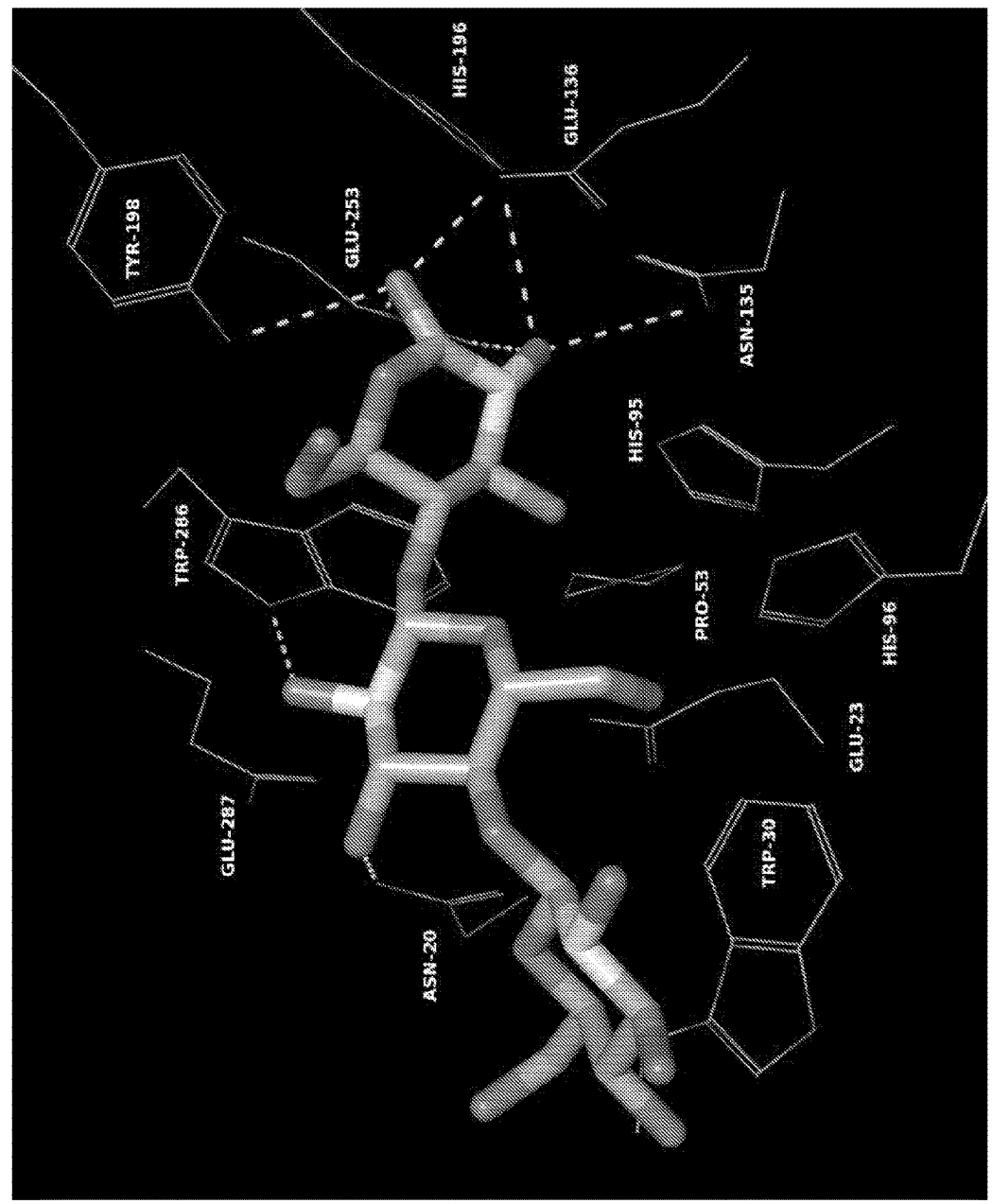

With this sequence alignment for family GH5 containing 681 sequences, we used FastTree to build a phylogenetic tree of the family. The GH5 tree is shown in FIG. 1 with the experimentally characterized functions culled from CAZy. This family was broken up into subfamilies by splitting along clades of the tree with significant bootstrap support and the names of the subfamilies (A1-A10) were matched to the clades using the presence of PDB structures.

The larger subfamilies identified from these clades correspond well to the divisions of different functions in the family: predominantly endoglucanase (A1, A2, and A5/6), predominantly mannanase (A7, A8, and A10) and predominantly licheninase (A9). Subfamily A4 containing Cel5ATma (142 genes) is the most functionally diverse, containing many endoglucanases, but it also has mannanases, endo-β-1,3-glucanases (3.2.1.6), endo-β-1,4-xylanases (3.2.1.8), 1,4-β-exoglucosidases (3.2.1.74), licheninases (3.2.1.73), and xyloglucan-specific endo-β-1,4-glucanases (3.2.1.151).

Choice of Cel5ATma

To dissect the mechanisms of specificity in this functionally diverse subfamily, we chose to focus on the dual-specificity enzyme Cel5ATma (accession id AAD36816.1) from *Thermotoga maritima*. This enzyme has activity on both cellulose and mannans comparable to or greater than single-specificity enzymes in this organism: Cel74 and Man5, respectively. In addition, both of these activities are functionally employed by *Thermotoga maritima*, which expresses the enzyme when it is grown on media containing either of these sugars.

Prediction and Characterization of Residues Altering Specificity

Figure 2:
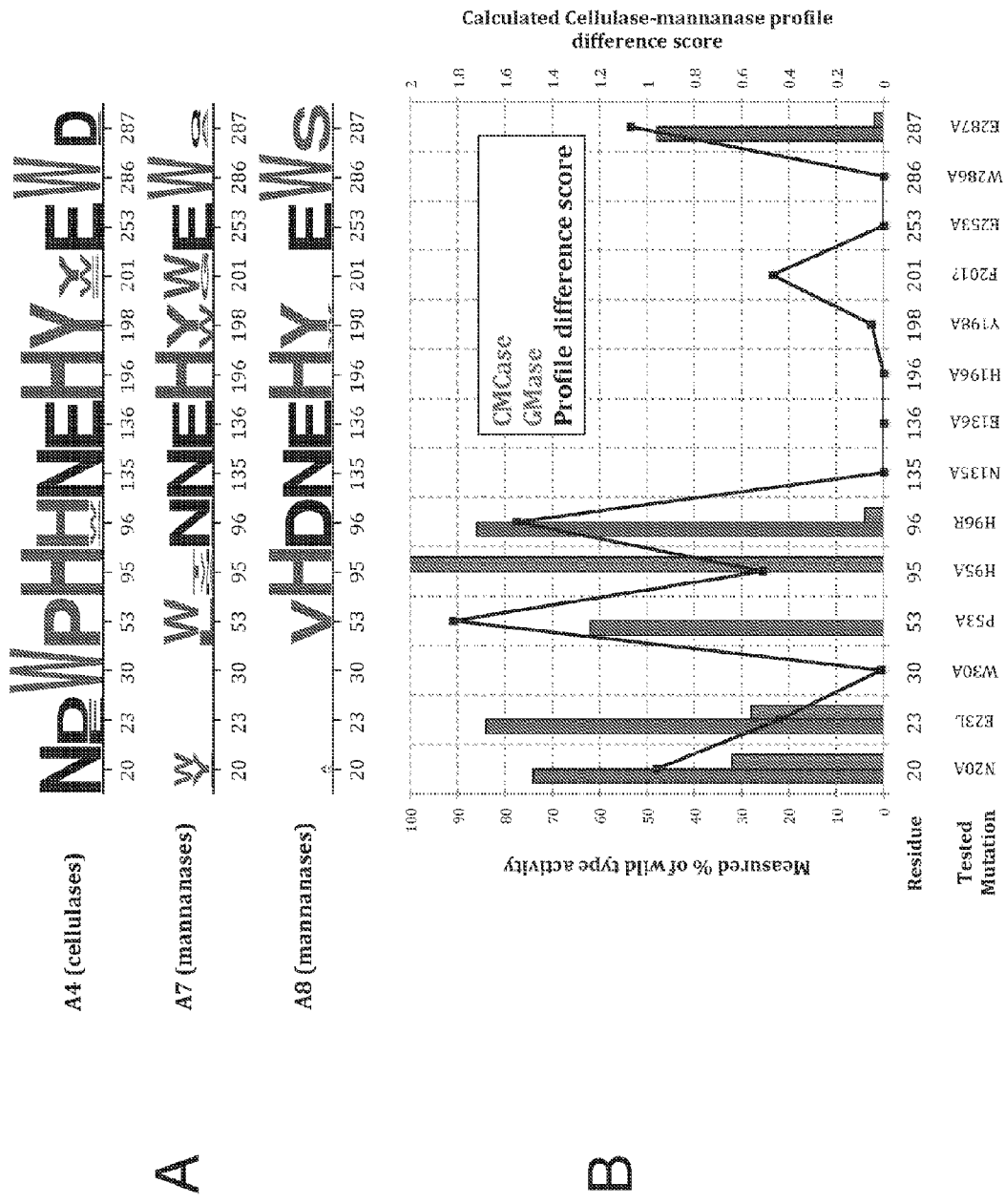
FIG. 2: (A) Sequence profiles for the active site positions in the GH5 subfamily containing Cel5ATma (A4, which is predominantly endoglucanase) and profiles of the two predominantly mannanase subfamilies (A7 and A8). (B) Plot of the BLOSUM-weighted score quantifying the differences in amino acid distributions at these positions between A4 and the combination of A7 and A8 (top). Experimental measurements of the activities of mutants at each position (bottom). Since multiple mutants were made for each residue from saturation and site-directed mutagenesis, the results for the mutants with the greatest specificity difference is shown for clarity.

To dissect the determinants of specificity in this enzyme, we looked for positions in the active site that differed between the mainly endoglucanase A4 subfamily and the two larger mostly mannanase subfamilies A7 and A8. This was done by taking the sequence alignments of genes in these and comparing the aligned active site positions from A4 to the combination of A7 and A8. The profile of amino acids at these positions is shown in FIG. 2A. To quantify the extent of the profile differences at each position we calculated the sum of the root mean squared BLOSUM-weighted difference for each amino acid and summed them (black line in FIG. 2B). For example, the catalytic glutamates at residues 136 and 253 are totally conserved, hence their scores are zero; however, position 96 has mainly histidines in subfamily A4 and mainly asparagines and aspartates in A7 and A8, resulting in a large difference score.

This analysis resulted in seven positions with large profile difference scores that we predicted could be involved in specificity. To test our predictions, we performed several mutational experiments. First, we did site directed mutagenesis on the Cel5ATma active site positions N20, E23, W30, P53, H95, H96, N135, E136, H196, Y198, F201, E253, W286, and E287. These positions were all mutated to alanine and the following conservative mutations were performed as well: N135D, E136D, E136Q, E253D, and E253Q. Each of the resulting site mutants was purified and assayed for CMCase and GMase activities.

In addition to the site-directed mutagenesis, we performed site-saturation mutagenesis at positions N20, E23, P53, H95, H96, F201, and E287 to explore the space of amino acids more thoroughly. These mutants were created using and assayed for CMCase and GMase activity in cell lysate. Mutants displaying specificity changes were sequenced, purified and assayed again for both activities.

FIG. 2B displays the experimentally determined CMCase and GMase activities for each of the active site positions, as well as their profile-difference scores. The data shown for each position are for the site-directed or the site-saturation mutation that exhibited the largest difference between the two activities. For the seven positions that had scores above 0.1 (20, 23, 53, 95, 96, 201, and 287), mutations at six of these positions (20, 23, 53, 95, 96, and 287) displayed altered specificity and for the seven positions (30, 135, 136, 196, 198, 253 and 286) that had scores lower than 0.1, no mutations exhibited altered specificity.

Prediction and Characterization of Dual-Specificity Genes in Subfamily A4

Figure 5:
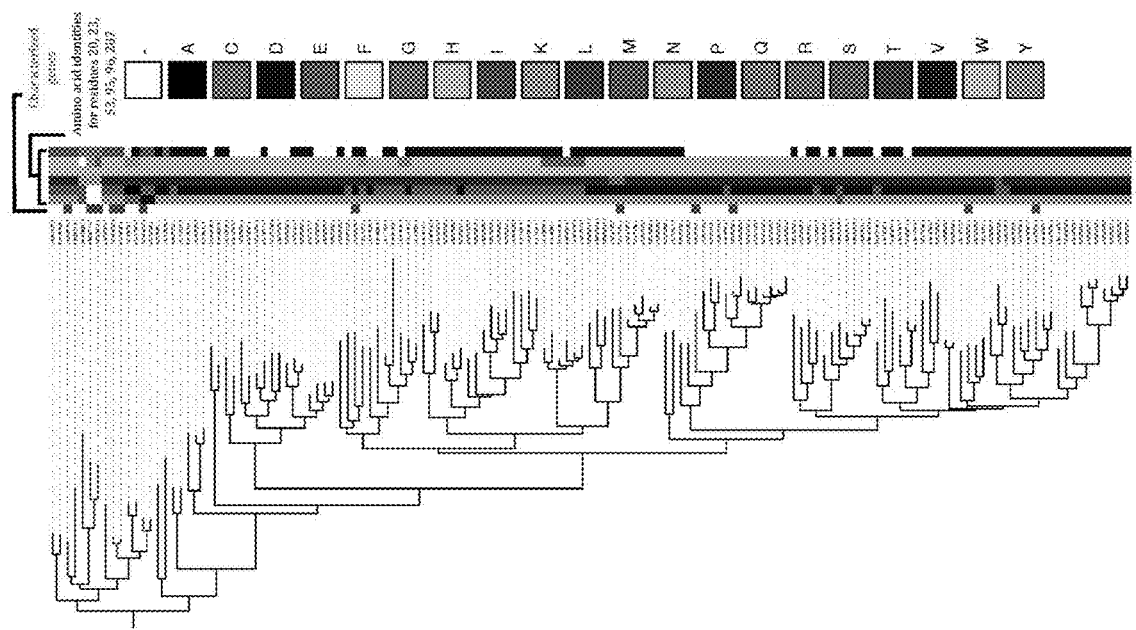
FIG. 5: Phylogenetic tree of GH5 subfamily A4 and the amino acid identities of the positions observed to confer specificity in Cel5ATma (N20, E23, H95, H96, and E287; $2^{nd}$ through $7^{th}$ colored columns). Genes characterized in this article for endoglucanase/mannanase activity are colored red in the tree and represented by red boxes in the first colored column.

Based on the above results describing six specificity-determining residues in Cel5ATma, we sought to determine if these patterns were generally true of the GH5 A4 subfamily. Although there were only a few genes in A4 that listed as experimentally characterized mannanases, there were many others with functions other than endoglucanase and mannanase. We hypothesized that since endoglucanase activity is the most commonly characterized activity in this subfamily, perhaps many of the studies had not assayed these enzymes for mannanase activity and that dual-specificity for cellulose and mannans could still be a common feature in this subfamily. To evaluate this idea, we looked at the pattern of amino acids at the six specificity-determining positions found in Ce5ATma (FIG. 5 block A). From this analysis we found that 77 genes of the 143 genes (54%) in our A4 subfamily phylogenetic tree that have the same or similar amino acids at the six specificity-determining positions as Cel5ATma. We predicted that these genes would be dual-specificity and those without this pattern would not have both endoglucanase and mannanase activities. As this pattern describes 54% of the subfamily, we predict that this dual-specificity was a general feature of the A4 subfamily.

Figure 3:
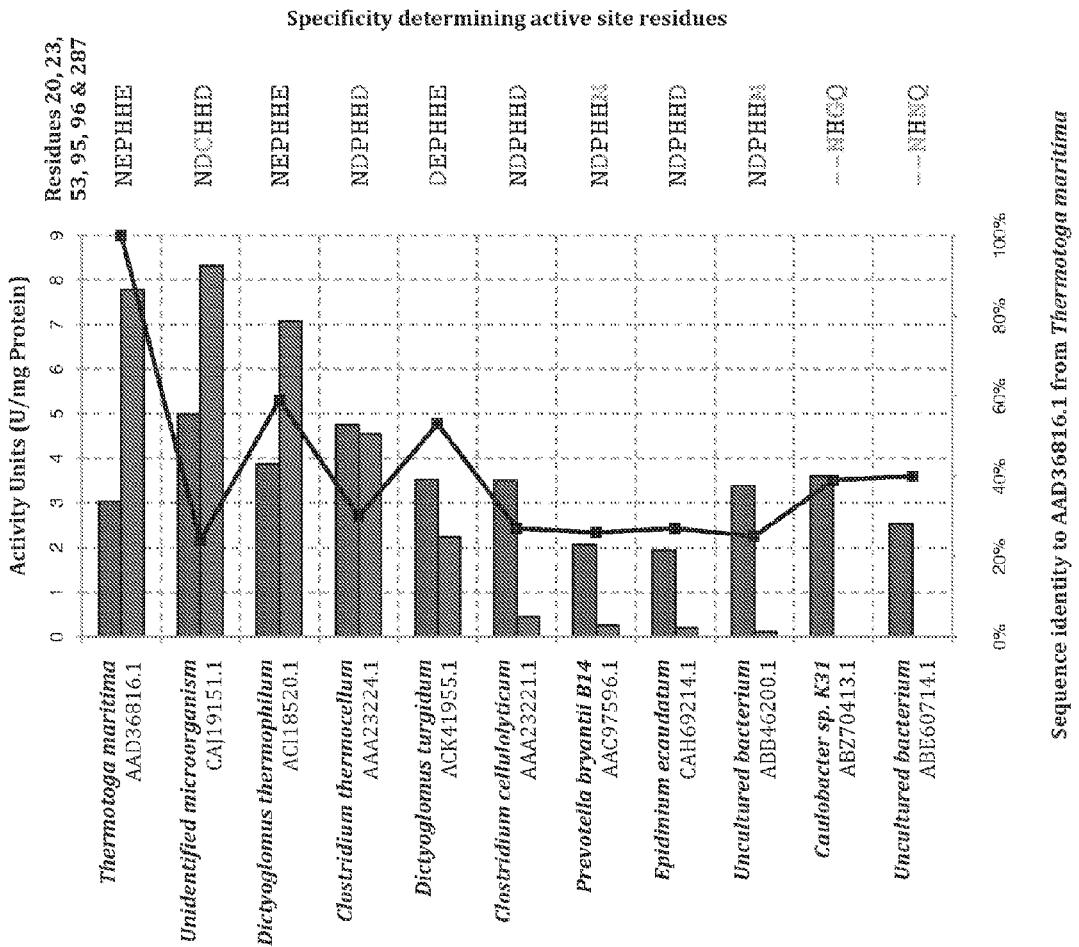
FIG. 3: Experimental characterization of the endoglucanase and mannanase activities of Cel5ATma and 11 other genes from GH5 subfamily A4. These genes were selected to broadly cover the A4 subfamily tree and to contain diversity at the specificity-determining positions. Sequence identity to Cel5ATma of each gene is depicted with a black line on the plot and the amino acid identities of the six specificity-determining positions are show at right.

To test the hypothesis that the six specificity-determining residues can predict whether genes in the A4 subfamily have dual-specificity and that dual-specificity in this subfamily is common, we selected 17 genes for characterization. These genes were selected to broadly cover the phylogenetic diversity in the A4 subfamily and to contain either similar or dissimilar amino acid patterns at the six specificity-determining positions. We describe a pattern as similar to the Cel5ATma pattern if the only differences are between glutamate and aspartate (which have the same functional group) or between asparagine and aspartate (which differ in the presence of nitrogen or oxygen in the functional group). Ten of these genes expressed and were soluble in our hands. FIG. 3 shows the CMCase and GMase activities in activity units per mg as well as the sequence identity of each gene to Cel5ATma and the amino acids at the six specificity-determining residues in Cel5ATma.

Each of the ten characterized genes had CMCase activity and seven (four) had GMase activity greater than 10% (20%) of the CMCase activity, confirming that dual-specificity is likely a common feature in the A4 subfamily. The characterized genes all had pairwise sequence identities below 70% and most had pairwise sequence identities below 40%. Two of these genes (from an unidentified microorganism and Clostridium thermocellum) were quite dissimilar from Cel5ATma with sequence identities less than or equal to 30%.

Of the five characterized genes with the same or highly similar amino acid pattern at the specificity-determining positions, five (three) had GMase activity greater than 10% (20%) of CMCase activity. Of the remaining five genes that had different patterns at these positions, two (one) had GMase activity greater than 10% (20%) of CMCase activity. One of the genes with significant activity on both substrates (CAJ19151.1 from an unidentified microorganism) had GMase activity higher than CMCase activity and contained a cysteine at position 53; thus, position 53 may not be a specificity determinant in the subfamily despite its relevance for specificity in Cel5ATma.

This data suggests that these residues are important for determining functional specificity in the A4 subfamily. Depending on the definition of dual-specificity in this case, all or a majority of the six enzymes with this pattern displayed some dual-specificity, as does Cel5ATma, while a majority of the five enzymes without this pattern displayed specificity for CMCase only.

Notably, four glycoside hydrolases in A4 subfamily also have xylanase activity, indicating that the residues noted above also contribute to the ability to hydrolyze xylose. The table below provides activity in units of activity/mg of enzyme.

|  | Specific activity (U/mg) | | |
| --- | --- | --- | --- |
| Enzymes | CMC | GM | BX |
| Cel5A_UI (M) | 5.00 | 8.33 | 4.70 |
| Cel5C_Cth (T) | 4.75 | 4.55 | 3.55 |
| Cel5A_Dth (T) | 3.89 | 7.08 | 0.74 |
| Cel5A_Dtu (T) | 3.66 | 6.04 | 0.84 |

Note:
CMC, carboxymethyl cellulose; GM, galactomannan; BX, birchwood xylan. M, mesophilic; T, thermophilic. These assays were at 60° C. and pH 5.50 (sodium citrate).

Validation of Specificity-Determining Residues in Sequence Divergent Genes

Figure 4:
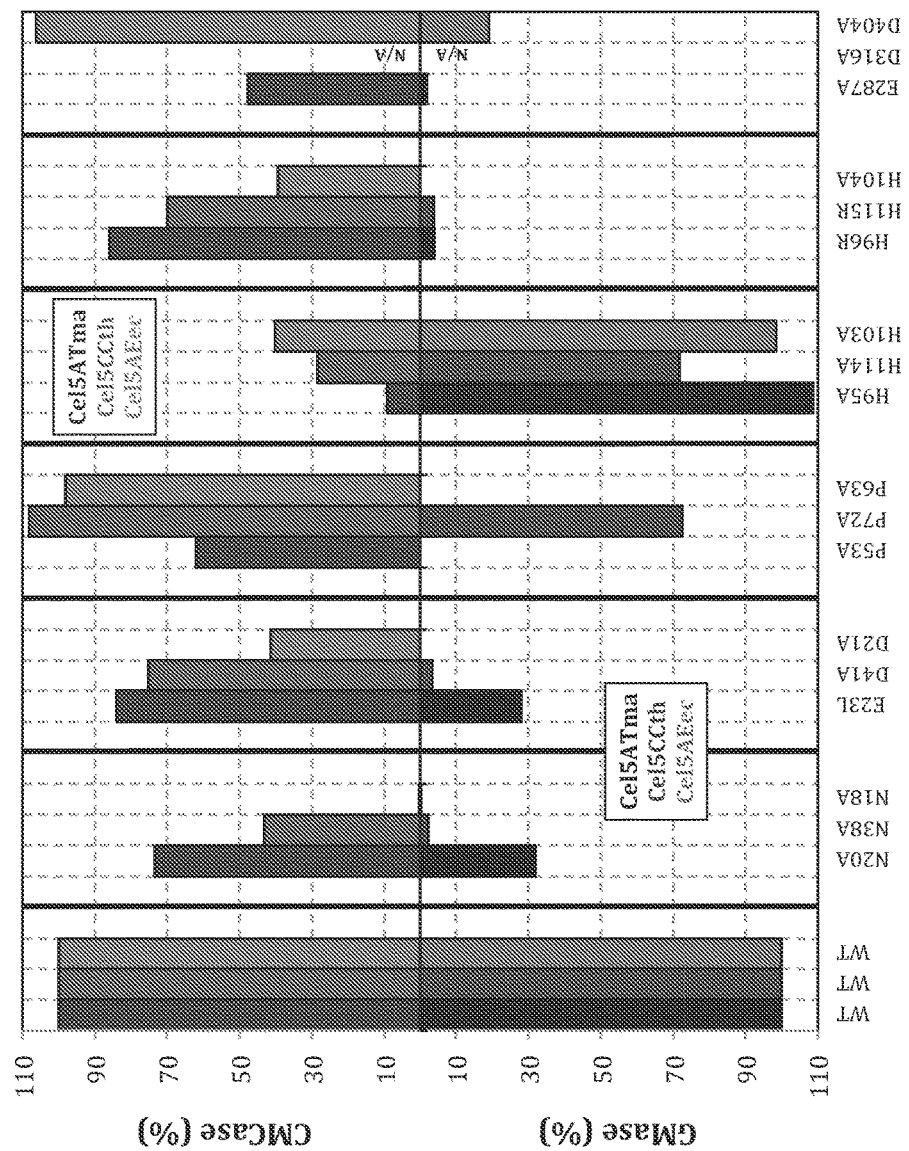
FIG. 4: CMCase and GMase activities relative to wildtype for mutants at the six specificity-determining positions described in the paper for Cel5ATma in comparison to Cel5Cth (30% sequence identity to Cel5ATma) and Cel5AEec (24% sequence identity to Cel5ATma).

To further test the hypothesis that these six residues are responsible for specificity across this subfamily we characterized the CMCase and GMase activities for alanine mutants at the six specificity-determining positions for two genes with low sequence identity to Cel5ATma: one gene with high CMase activity and GMase activity (Cel5CCth, AAA23224.1 from Clostridium thermocellum) and one gene with high CMCase activity and low GMase activity (Cel5AEec, CAH69214.1 from Epidinium ecaudatum). As show in FIG. 4, the specificity changes in Cel5CCth resulting from the mutations N38A, D41A, and H115R show large reductions in GMase activity while maintaining significant CMCase activity, and the mutation H114A predominantly reduces the CMCase activity while maintaining most of the GMase activity. These results match closely the corresponding pattern in the specificity changes resulting from the Cel5ATma mutations N20A, E23L, H96R, and H95A, respectively. Alanine mutants at P72 and D316 of Cel5CCth (corresponding to P53 and E287 in Cel5ATma) did not show a large specificity change and was not able to be stably expressed, respectively. However, perhaps saturation mutagenesis—as was done for CelATma—at these positions would have given different results. For Cel5AEec, the mutations D21A, P63A, H104A and D404A effectively reduced GMase activity to zero while maintaining significant CMCase activity, and H103A had a measurable effect of CMCase activity while maintaining GMase activity. These results as well show a pattern of specificity changes similar to the corresponding mutations in Cel5ATma of E23L, P53A, H96A, E287A and H95A, respectively. Additional data is provided in the table below.

Mutations of the Motif in Cel5_CCth

|  | Relative activity (%) | | |
| --- | --- | --- | --- |
| Cel5C_Cth | CMC | GM | BX |
| WT | 100 | 100 | 100 |
| N38A | 43.23 | 2.35 | 0.14 |
| D41A | 75.2 | 3.35 | 0.63 |
| P72A | 108.25 | 72.49 | 118.46 |
| H114A | 28.46 | 71.62 | 6.42 |
| H115R | 69.92 | 3.81 | 0.98 |
| D316A* | N.A. | N.A. | D.A. |

Note:
CMC, carboxymethyl cellulose; GM, galactomannan; BX, birchwood xylan. M, mesophilic; T, thermophilic. These assays were at 60° C. and pH 5.50 (sodium citrate).

As further evidence that the residues identified confer promiscuity, we introduced the D14N (GAT→AAT) amino acid change to Cel5BDtu (SEQ ID NO:8) such that the resulting enzyme had increased cellulase and mannanse activity compared to the parent sequence.

Engineered Dual-Specific GH5-Ce15B_Dtu

| Sub- | | Cel5B_Dtu | | Improve- |
| --- | --- | --- | --- | --- |
| strate | Activity parameters | WT | D14N | ment (%) |
| CMC | S.A. (U · mg$^{-1}$ protein) | 28.89 ± 0.96 | 50.03 ± 0.97 | 73.17 |
|  | $k_{cat}$ (s$^{-1}$) | 408.19 | 550.66 | 34.90 |
|  | $K_m$ (mg · ml$^{-1}$) | 24.02 | 11.76 | 104.25 |
|  | $k_{cat}/K_m$ (ml · mg$^{-1}$ · s$^{-1}$) | 17.00 | 46.81 | 175.35 |
| CGM | S.A. (U · mg$^{-1}$ protein) | 2.11 ± 0.03 | 8.83 ± 0.36 | 318.48 |
|  | $k_{cat}$ (s$^{-1}$) | 68.25 | 71.82 | 5.24 |
|  | $K_m$ (mg · ml$^{-1}$) | 11.57 | 0.72 | 1506.94 |
|  | $k_{cat}/K_m$ (ml · mg$^{-1}$ · s$^{-1}$) | 5.90 | 99.89 | 1593.05 |

Note:
CMC, carboxymethyl cellulose; CGM, carob galactomannan. These assays were at 70° C. and pH 5.00 (sodium citrate) for CMC; 75° C. and pH 5.50 (sodium citrate) for GM.

Discussion

The computational predictions and mutational experiments described in this study have enabled us to identify several specificity-determining residues in a dual-specificity enzyme, Cel5ATma from *Thermotoga maritima*. From these predicted and characterized specificity-determining residues, we were able to find numerous dual-specificity genes across this functionally diverse subfamily. This data suggests that dual-specificity is a common feature of this subfamily, an observation that has not previously been described to our knowledge.

We have shown that these residues are similarly important for determining specificity in two genes that have low sequence identity to Cel5ATma. The fact that these three distantly related genes show similar patterns of specificity at these residues indicates that these positions are determinants of specificity across this diverse subfamily.

Materials and Methods
Chemicals and Reagents

All chemicals and enzymes were analytical grade from Sigma or EMD Chemicals. BugBuster Protein Extraction Reagent, Popculture Reagent, rLysozyme solution, Benzonase Nuclease HC (Purity >90%) and Proteinase inhibitor Cocktail V (EDTA-free) were from Novagen and Calbiochem (EMD Biosciences). Champion pET101 Directional TOPO Expression Kit was purchased from Invitrogen. Ni-NTA Spin Columns were purchased from Qiagen. Zeba Spin Desalting Columns (2 ml, 7 k MWCO) were from Pierce (Thermo Fisher Scientific). Bicinchoninic Acid Kit (BCAI-1KT) was from Sigma-Aldrich. Luria-Bertani (LB) media were from EMD Chemicals and 2xYT medium from Sigma-Aldrich.

Gene Synthesis and Cloning

Genes were codon-optimized according to the codon usage in *E. coli* and synthesized by Genescript USA, Inc. All the genes were amplified and cloned by pCDF-2 Ek/LIC vector kit (Novagen, EMD Biosciences) except that cel5aPbr was cloned into pET101 vector (Invitrogen). Cloning primers are listed in Supplement Materials. Construct for cel5aTma, pCDF2-cel5aTma was described before. All the constructs were confirmed by DNA sequencing (Quintara).

Protein Expression and Purification

All the constructs were transformed into BL21 (DE3) (Novagen, EMD Biosciences) for protein expression. Single colonies were inoculated into 5 ml LB autoinduction media (Overnight Express Autoinduction System 1, Novagen, EMD Biosciences) containing appropriate antibiotics (100 µg/ml of carbenicillin for pET101 constructs while 100 µg/ml of streptomycin for the others) and incubated at 30° C. for 24 hr. Induced cultures were harvested and preserved at −80° C. until use. Protein extraction, purification, buffer exchange and concentration determination were as described before.

Enzyme Assays

For the enzymes except Cel5ATma and its mutants, mesophilic enzymes were assayed at 37° C. while thermophilic ones at 60° C. 50 mM sodium citrate buffer (pH 5.50) was used for these enzyme reactions. Enzyme assays for Cel5ATma and its mutants were performed at 70° C. and pH 5.0 for cellulase activity while 90° C. and pH 5.5 for mannanase activity. Buffering system was 50 mM sodium citrate. The enzyme reactions contained 0.5% carboxymethyl cellulose (CMC) and locus bean gum (LBG) as substrates for cellulase and mannanase assays, respectively. Reducing sugars were determined by DNS method as described before. D-glucose and D-mannose (0-5 mM) were used as standards for reducing sugars when assaying cellulase and mannanase, respectively. One unit of cellulase or mannanase activity is defined as the amount of enzyme required for producing 1 µmol of reducing sugars per minute.

Mutagenesis and Libraries Screening

Site-directed mutagenesis (SDM) and site-saturation mutagenesis (SSM) were conducted by using QuikChange Lightning Site-Directed Mutagenesis Kit according to the instructions of manufacturer (Stratagene, Agilent Technologies). All mutagenic primers are listed in Supplement Materials. The mutant plasmids were extracted by QIAprep Spin Miniprep Kit (Qiagen) and confirmed by DNA sequencing.

SSM libraries were screened by the high throughput screening system developed recently [2]. For mannanase activity screening, LBG and 50 mM sodium citrate (pH 5.50) were used as substrate and buffer, and reaction time was extended to one hour compared with cellulase assays.

Creation of Structure-Based Sequence Alignment

To build a high quality sequence alignment in this diverse protein family, we used a combination of structural and sequence information. First, we performed pairwise structural alignments with 3Dhit of 22 GH5 family structures (chain A of pdb ids 2JEP, 3L55, 1BQC, 2WHL, 7A3H, 2OSX, 1H1N, 1QNR, 1TVN, 1RH9, 1UUQ, 1EDG, 2COH, 2CKS, 1WKY, 1H4P, 2PC8, 1CEO, 2ZUM, 1VJZ, 1EGZ, and 1ECE) to the Cel5ATma structure (pdb id 3MMW, chain A). These 23 structures were selected based on their resolution and to remove redundancy at 90% sequence identity. For each of these structures, we performed BLAST on the GH5 sequences (after removing short sequence fragments) from the carbohydrate active enzymes database (CAZy) to find sequences between 25% and 90% sequence identity of the structure's sequence and the resulting sequences were aligned with MUSCLE. These 23 multiple sequence alignments were then combined into one large sequence alignment by aligning equivalent positions in the individual sequence alignments using the pairwise structural alignments to 3MMWA. Redundant sequences were filtered out at 90% sequence identity, preferentially keeping sequences with structures, experimental characterization and longer lengths, in this order of priority.

Note: In FIG. 1, the annotated experimental characterization from CAZy of AAA71887.1 was changed to 3.2.1.78 only and the characterization of ABB46200.1 was changed to 3.2.1.4 only because these genes both contain multiple domains, only one of which was a member of GH5. We used the structural alignment of AAC97596.1 (PDB id 3L55) to decide that the sequence alignment around positions 287 in genes AAC97596.1 and ABB46200.1 was inaccurate and should be methionines instead of gaps (FIG. 3).

Creation of the Phylogenetic Tree

Gappy positions and their neighbors were trimmed from the above structure-based sequence alignment by removing positions with less than 60% occupancy and two flanking positions. A tree was built from the resulting trimmed alignment using FastTree 2.1.3.

Subfamily Identification

Subfamilies were divided based on the clade divisions in the tree with high bootstrap support above 80% (FIG. 1) and were named using the literature designations in the crystal structure references that contained the subfamily designations.

Selection of Cel5Tma Active Site Residues for Analysis

The ligand in 1ECE was used to find active site positions because this ligand represents a 4 sugar substrate on both sides of the active site, whereas most other cocrystals of homologs contain ligands binding to only side of the active site. Residues with side chain atoms with 6A of the 1ECE ligand were selected with the exception of A24, which is pointing away from the active site. Residues with sequence entropy in the A4 subfamily of the MSA greater than 1.75 and occupancy less than 70% were removed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated recombinant glycoside hydrolase that is a variant of a native GH5 A4 subfamily glycoside hydrolase, wherein the variant glycoside hydrolase:

(i) has increased cellulase and/or mannanase activity compared to the native GH5 A4 subfamily glycoside hydrolase, (ii) has at least 95% amino acid sequence identity to the native GH5 A4 subfamily glycoside hydrolase, and (iii) comprises the following amino acids at positions in the native GH4A4 subfamily glycoside hydrolase that correspond to positions 20, 23, 53, 95, 96, and 287 of SEQ ID NO:1:

asparagine at position 20,
aspartic acid or glutamic acid at position 23,
proline at position 53,
histidine at position 95,
histidine at position 96 and
aspartic acid or glutamic acid at position 287,
wherein at least one of the amino acid residues at position 20, 23, 53, 95, 96, and 287 is substituted for another amino acid as compared to the amino acid that is present at that position in the native GH4A4 subfamily glycoside hydrolase.

2. The recombinant glycoside hydrolase of claim 1, wherein the recombinant glycoside hydrolase has a cellulase activity and/or mannanase activity at least 10% higher than the activity of glycoside hydrolase of the native GH5 A4 subfamily glycoside hydrolase.

3. The recombinant glycoside hydrolase of claim 1, wherein the variant glycoside hydrolase has cellulase activity, xylanase activity, and mannanase activity.

4. The recombinant glycoside hydrolase of claim 1, wherein the variant glycoside hydrolase has at least 95% amino acid sequence identity to any one of SEQ ID NOS:5, 7, or 9.

5. A method of generating free sugars from a mixture comprising cellulose and mannan, the method comprising contacting the mixture with a glycoside hydrolase of claim 1 under conditions such that the glycoside hydrolase hydrolyzes the at least two polymeric substrates, thereby generating free sugars.

6. The method of claim 5, wherein the mixture comprises cellulose, xylan and mannan and the glycoside hydrolase hydrolyzes each of the cellulose, xylan and mannan.

7. The method of claim 5, wherein the variant glycoside hydrolase has at least 95% amino acid sequence identity to any one of SEQ ID NOS:5, 7, or 9.

8. The recombinant glycoside hydrolase of claim 1, wherein the variant glycoside hydrolase has at least 95% identity to SEQ ID NO:9.

\* \* \* \* \*